US008361464B2

(12) United States Patent
Griffiths et al.

(10) Patent No.: US 8,361,464 B2
(45) Date of Patent: Jan. 29, 2013

(54) ANTHRACYCLINE-ANTIBODY CONJUGATES FOR CANCER THERAPY

(75) Inventors: Gary L. Griffiths, North Potomac, MD (US); Hans J. Hansen, Picayune, MS (US); Zhengxing Qu, Warren, NJ (US); David M. Goldenberg, Mendham, NJ (US)

(73) Assignee: Immunomedics, Inc., Morris Plains, NJ (US)

( * ) Notice: Subject to any disclaimer, the term of this patent is extended or adjusted under 35 U.S.C. 154(b) by 0 days.

(21) Appl. No.: 12/564,335

(22) Filed: Sep. 22, 2009

(65) Prior Publication Data

US 2010/0074840 A1   Mar. 25, 2010

Related U.S. Application Data

(60) Continuation-in-part of application No. 11/137,385, filed on May 26, 2005, which is a continuation of application No. PCT/US2004/001367, filed on Jan. 20, 2004, application No. 12/564,335, which is a continuation-in-part of application No. 11/754,902, filed on May 29, 2007, which is a division of application No. 10/377,122, filed on Mar. 3, 2003, now Pat. No. 7,312,318.

(60) Provisional application No. 60/442,125, filed on Jan. 24, 2003, provisional application No. 60/360,259, filed on Mar. 1, 2002.

(51) Int. Cl.
*A61K 39/395* (2006.01)
*A61K 51/00* (2006.01)

(52) U.S. Cl. ............... 424/133.1; 424/172.1; 424/178.1; 424/181.1

(58) Field of Classification Search ............... 424/133.1, 424/172.1, 178.1, 181.1
See application file for complete search history.

(56) References Cited

U.S. PATENT DOCUMENTS

| 4,816,567 | A |   | 3/1989  | Cabilly et al.              |
|-----------|---|---|---------|------------------------------|
| 5,521,290 | A | * | 5/1996  | Sivam et al. ........ 530/391.5 |
| 5,530,101 | A | * | 6/1996  | Queen et al. ........ 530/387.3 |
| 5,618,920 | A |   | 4/1997  | Robinson et al.              |
| 5,693,762 | A |   | 12/1997 | Queen et al.                 |
| 5,708,146 | A |   | 1/1998  | Willner et al.               |
| 5,736,137 | A |   | 4/1998  | Anderson et al.              |
| 5,846,534 | A | * | 12/1998 | Waldmann et al. ........ 424/133.1 |
| 6,051,230 | A |   | 4/2000  | Thorpe et al.                |
| 6,653,104 | B2 |  | 11/2003 | Goldenberg et al.            |
| 7,151,164 | B2 |  | 12/2006 | Hansen et al.                |
| 7,312,318 | B2 | * | 12/2007 | Hansen et al. ........ 530/387.3 |
| 7,534,427 | B2 | * | 5/2009  | Goldenberg et al. ........ 424/130.1 |
| 7,772,373 | B2 | * | 8/2010  | Hansen et al. ........ 530/387.7 |
| 7,829,064 | B2 | * | 11/2010 | Griffiths et al. ........ 424/1.21 |
| 2002/0018749 | A1 |   | 2/2002 | Hudson et al.               |
| 2004/0115193 | A1 | * | 6/2004 | Hansen et al. ........ 424/141.1 |

FOREIGN PATENT DOCUMENTS

| EP | 0476408 |      | 3/1992  |
|----|---------|------|---------|
| EP | 0476408 | A1 * | 3/1992  |
| EP | 0495265 |      | 7/1992  |
| EP | 0624377 |      | 11/1994 |
| EP | 0665020 |      | 8/1995  |
| WO | WO92/01059 | * | 1/1992 |
| WO | 97/23243 |   | 7/1997  |
| WO | 98/50435 |   | 11/1998 |
| WO | 00/67795 |   | 11/2000 |
| WO | 00/74718 |   | 12/2000 |
| WO | WO 0074718 | A1 * | 12/2000 |
| WO | 03/074566 |   | 9/2003 |
| WO | 03/074567 |   | 9/2003 |

OTHER PUBLICATIONS

Michel et al. (Clinical Cancer Research 2005; 11: 777-786).*
Froesch et al. (Cancer Immunol. Immunother. 1996; 42: 55-63.*
Sapra et al. (Clin. Cancer. Res. 11(4):5257-5264 (2005)).*
Griffiths et al. (Clin. Can. Res.9:6567-6571 (2003)).*
Voskoglou-Nomikos (Clin. Can. Res. 9:4227-4239 (2003)).*
Dennis (Nature 442:739-741 (2006)).*
Cespdes et al. (Clin. Transl. Oncol. 8(5):318-329 (2006)).*
Talmadge et al. (Am. J. Pathol 170(3):793-804 (2007)).*
Fujimori et al. (J. Nuc. Med. 31:1191-1198 (1990)).*
Beckman et al. (Can. 109:170-179 (2007)).*
Thurber et al. (Adv. Drug Deliv. Rev. 60:1421-1434 (2008)).*
Rudnick et al. (Can. Biotherp. & Radiopharm. 24: 155-162 (2009)).*
Alinari et al. (Blood 117:4530-4541; Jan. 12, 2011).*
Berkova et al. (Expert. Opin. Invest. Drugs 19(1):141-149 (2010)).*
Gold et al. (Int. J. Clin. Exp. Pathol. 4(1):1-12 (2011)).*
Moore and Sodroski (J. Virol. 70(3):1863-1872 (1996)).*
Shi et al. (J. Immunol. Methods 314:9-20 (2006)).*
van der Geld et al. (Clin. Exp. Immunol. 118:487-496 (1999)).*
Human Protein Reference Database datasheet for CD74; pp. 1-2; Oct. 12, 2011.*
HPRD.org, data sheet for "CD74"; pp. 1-2; Jan. 24, 2012.*
Bendig, M., "Humanization of Rodent Monoclonal Antibodies by CDR Grafting", Academic Press Inc., New York, NY, vol. 8, (1995), pp. 83-93.
Brambilla et al., "Phase II study of doxorubicin versus epirubicin in advanced breast cancer", Cancer Treat Rep. Feb. 1986;70(2):261-6.
Burgess et al., "Possible dissociation of the heparin-binding and mitogenic activities of heparin-binding (acidic fibroblast) growth factor-1 from its receptor-binding activities by site-directed mutagenesis of a single lysine residue", J. Cell Biol. 111:2129-2138 (1990).
Colman, P., "Effects of amino acid sequence changes on antibody-antigen interactions", Res. Immunol. 1994, 145:33-36.

(Continued)

*Primary Examiner* — Lynn Bristol
(74) *Attorney, Agent, or Firm* — Richard A. Nakashima

(57) ABSTRACT

The invention relates to therapeutic conjugates with the ability to target various antigens. The conjugates contain a targeting antibody or antigen binding fragment thereof and an anthracycline chemotherapeutic drug. The targeting antibody and the chemotherapeutic drug are linked via a linker comprising a hydrazide moiety.

8 Claims, 14 Drawing Sheets

OTHER PUBLICATIONS

Di Stefano et al., "A novel method for coupling doxorubicin to lactosaminated human albumin by an acid sensitive hydrazone bond: synthesis, characterization and preliminary biological properties of the conjugate", Eur. J. Pharm. Sci. 23:393-397 (2004).

Froesch et al., "Preparation and functional evaluation of new doxorubicin immunoconjugates containing an acid-sensitive linker on small-cell lung cancer cells", Cancer Immunol Immunother. Jan. 1996;42(1):55-63.

Gondo et al., "HLA class II antigen associated invariant chain gene expression in malignant lymphoma", Br. J. Haematol. Dec. 1987;67(4):413-7.

Griffiths et al., "Cure of SCID mice bearing human B-lymphoma xenografts by an anti-CD74 antibody-anthracycline drug conjugate", Clin Cancer Res. Dec. 15, 2003;9(17):6567-71.

Griffiths et al., "Promising Therapeutic Activity of a New Drug Immunoconjugate, IMMU-110, in a Human Burkitt Lymphoma Model", Blood Nov. 16, 2003;102(11):645A, Abstract # 2381.

Hansen et al., "Internalization and catabolism of radiolabelled antibodies to the MHC class-II invariant chain by B-cell lymphomas", Biochem. J. 1996, 320:293-300.

Ibragimova et al., "Stability of the beta-sheet of the WW domain: A molecular dynamics simulation study", Biophys. J. Oct. 1999;77(4):2191-8.

Kaneko et al., "New hydrazone derivatives of adriamycin and their immunoconjugates—a correlation between acid stability and cytotoxicity", Bioconjug Chem. May-Jun. 1991;2(3):133-41.

King et al., "BR96 conjugates of highly potent anthracyclines", Bioorg Med Chem Lett. Jul. 7, 2003;13(13):2119-22.

King et al., "Monoclonal antibody conjugates of doxorubicin prepared with branched linkers: A novel method for increasing the potency of doxorubicin immunoconjugates", Bioconjug Chem. Mar.-Apr. 1999;10(2):279-88.

Kolata, G., "Clinical promise with new hormones", Science 236:517-519 (1987).

Lambert, J., "Drug-conjugated monoclonal antibodies for the treatment of cancer", Curr Opin Pharmacol. Oct. 2005;5 (5):543-9.

Lau et al., "Novel doxorubicin-monoclonal anti-carcinoembryonic antigen antibody immunoconjugate activity in vitro", Bioorg Med Chem. Oct. 1995;3(10):1305-12.

Lazar et al., "Transforming growth factor alpha: an aromatic side chain at position 38 is essential for biological activity", Mol. Cell. Biol. 8(3):1247-1252 (1988).

Michel et al., "Therapy of small subcutaneous B-lymphoma xenografts with antibodies conjugated to radionuclides emitting low-energy electrons", Clin Cancer Res. Jan. 15, 2005;11(2 Pt 1):777-86.

Moller et al., "CD74", J. Biol. Regul. Homeost. Agents Oct.-Dec. 2000;14(4):299-301.

Mueller et al., "Antibody conjugates with morpholinodoxorubicin and acid-cleavable linkers", Bioconjug Chem. Sep.-Oct. 1990;1(5):325-30.

Nagy et al., "High yield conversion of doxorubicin to 2-pyrrolinodoxorubicin, an analog 500-1000 times more potent: structure-activity relationship of daunosamine-modified derivatives of doxorubicin", Proc Natl Acad Sci U S A. Mar. 19, 1996;93(6):2464-9.

Ochakovskaya et al., Therapy of Disseminated B-Cell Lymphoma Xenografts in Severe Combined Immunodeficient Mice with an Anti-CD74 Antibody Conjugated with (111)Indium, (67)Gallium, or (90)Yttrium, Clin. Cancer Res. 7(6):1505-1510 (2001).

Orlandi et al., "Cloning immunoglobulin variable domains for expression by the polymerase chain reaction", Proc. Natl. Acad. Sci. USA 86:3833-3837 (1989).

Oster et al., "Erythropoietin for the Treatment of Anemia of Malignancy Associated with Neoplastic Bone Marrow Infiltration", J. Clin. Oncol., 8(6):956-962 (1990).

Qu et al, "Internalization and Cytotoxic Effects of a Humanized Anti-CD74 Antibody, LL1", Proc. Am. Assoc. Cancer Res 2002;43:255.

Rudikoff et al., "Single amino acid substitution altering antigen-binding specificity", Proc. Natl. Acad. Sci. USA 1982; 79(6):1979-83.

Sapra et al., "Anti-CD74 Antibody-Doxorubicin Conjugate, IMMU-110, in a Human Multiple Myeloma Xenograft and in Monkeys" Clin Cancer Res. Jul. 15, 2005;11(14):5257-64.

Scott et al., "Synthesis of reagents for the one step incorporation of hydrazide functionality onto the lysine residues of proteins, and their use as linkers for carbonyl containing molecules", Bioorg Med Chem Lett. 6(13):1491-1496 (1996).

Shih et al. "Localization of an antibody to CD74 (MHC class II invariant chain) to human B cell lymphoma xenografts in nude mice", Cancer Immunol. Immunother. 49:208-216 (2000).

Trail et al., "Cure of Xenografted Human Carcinoma by BR96-Doxorubicin Immunoconjugates", Science Jul. 9, 1993;261(5118):212-5.

Tutt et al., "Monoclonal Antibody Therapy of B Cell Lymphoma: Signaling Activity on Tumor Cells Appears More Important Than Recruitment of Effectors", J. Immunol. 161(6):3176-85 (1998).

Willner et al., "(6-Maleimidocaproyl)hydrazone of doxorubicin—a new derivative for the preparation of immunoconjugates of doxorubicin", Bioconjug Chem. Nov.-Dec. 1993;4(6):521-7.

Zwirner et al., "MICA, a new polymorphic HLA-related antigen, is expressed mainly by keratinocytes, endothelial cells, and monocytes", Immunogenetics. 1998;47(2):139-48.

* cited by examiner

FIG. 6A

```
              1                 10              20              30           40
RF-TS3        QVQLVQSGSELKKPGASVKVSCKASGYTFTSYAMNWVRQA
cLL1VH        QVQLQ···P·····ET···T······N·GV··IK··T
hLL1VH        QVQLQQSGSELKKPGASVKVSCKASGYTFTNYGVNWIKQA 50 52 A                60              70
RF-TS3        PGQGLEWMGWINTNTGNPTYAQGFTGRFVFSLDTSVSTAY
cLL1VH        ··E···Q······P···E··FDDD····A···ES·A··F
hLL1VH        PGQGLQWMGWINPNTGEPTFDDDFTGRFAFSLDTSVSTAY 80 82 A B C        90             100 A B K
RF-TS3        LQISSLKADDTAVYYCAREDSNGYKIFDY
cLL1VH        ···N··NE·MGT·F·S·SRGKNEAW·A·
hLL1VH        LQISSLKADDTAVYFCSRSRGKNEAWFAY 103        110 113
NEWM          WGQGSLVTVSS
cLL1VH        ····T··TVSS
hLL1VH        WGQGSLVTVSS
```

FIG. 6B

```
             1         10        20        27 A B C D E   30
HF-21/28  DVVMTQSPLSLPVTLGQPASISCRSSQSLVHSDGNTYLNW
cLL1Vk    DIQL··T·····S·DQ···········RN·····H
hLL1Vk    DIQL··T·····S·DQ···········RN·····H 40        50        60        70
HF-21/28  FQQRPGQSPRRLIYKVSNRDSGVPDRFSGSGSGTDFTLKI
cLL1Vk    YL····KL···T·F··························
hLL1Vk    ······L···T·F··························

80        90       100       108
HF-21/28  SRVEAEDVGVYYCMQGTHWPFTFGQGTRLEI--
cLL1Vk    ········L·F·S·SS·V·P·A··K····IKR
hLL1Vk    ········F·S·SS·V·P·A·····IKR
```

FIG. 7A

```
CAGGTCCAACTGCAGCAATCTGGGTCTGAGTTGAAGAAGCCTGGGGCCTCAGTGAAGGTTTCCTGCAAGGCTTCACT      90
    ---------+---------+---------+---------+---------+---------+---------+
GTCCAGGTTGACGTCGTTAGACCCAGACTCAACTTCTTCGGACCCCGGAGTCACTTCCAAGGACGTTCCGAAGACCTATGTGGAAGTGA

Q  V  Q  L  Q  Q  S  G  S  E  L  K  K  P  G  A  S  V  K  V  S  C  K  A  S  G  Y  T  F  T    30

AACTATGGAGTGAACTGGATAAAGCAGGCCCCTGGACAAGGGCTTGAGTGGATGGGCTGGATAAACCCCAACACTGGAGAGCCAACATTT    180
   ---------+---------+---------+---------+---------+---------+---------+---------+
TTGATACCTCACTTGACCTATTTCGTCCGGGGACCTGTTCCCGAACTCACCTACCGACCTATTTGGGGTTGTGACCTCTCGGTTGTAAA

N  Y  G  V  N     W  I  K  Q  A  P  G  Q  G  L  Q  W  M  G     W  I  N  P  N  T  G  E  P  T  F    59
  CDR1                                                         CDR2

GATGATGACTTCAAGGGACGATTTGCCTTCTCCTTGGACACCTCTGTCAGCAGCACATATCTCCAGATCAGCAGCCTAAAGGCTGACGAC    270
   ---------+---------+---------+---------+---------+---------+---------+---------+
CTACTACTGAAGTTCCCTGCTAAACGGAAGAGGAACCTGTGGAGACAGTCGTCGTGTATAGAGGTCTAGTCGTCGGATTTCCGACTGCTG

D  D  D  F  K  G     R  F  A  F  S  L  D  T  S  V  S  S  T  Y  L  Q  I  S  S  L  K  A  D  D    89

ACTGCCGTGTATTTCTGTGTTCAAGATCGAGGGGTAAAAACGAAGCCTGGTTTGCTTATTGGGGCCAAGGGACCCTGGTCACCGTCTCCTCA    360
   ---------+---------+---------+---------+---------+---------+---------+---------+
TGACGGCACATAAAGACAAGTTCTAGCTCCCCATTTTTGCTTCGGACCAAACGAATAACCCCGGTTCCCTGGGACCAGTGGCAGAGGAGT

T  A  V  Y  F  C  S  R     S  R  G  K  N  E  A  W  F  A  Y     W  G  Q  G  T  L  V  T  V  S  S    113
                             CDR3
```

FIG. 7B

```
GACATCCAGCTGACTCAGTCTCCACTCTCCCTGCCCGTCACCCTTGGACAGCCTGCCTCCATCTCCTGCAGATCAAGTCAGAGCCTTGTA        90
        ----+----+----+----+----+----+----+----+----+----+----+----+----+----+----+----+----+----+
CTGTAGGTCGACTGAGTCAGAGGTGAGAGGGACGGGCAGTGGGAACCTGTCGGACGGGAGGTAGAGACGTCTAGTTCAGTCTCGGAACAT
 D  I  Q  L  T  Q  S  P  L  S  L  P  V  T  L  G  Q  P  A  S  I  S  C  R  S  S  Q  S  L  V       28C
                                                                            CDR1

CACAGAAATGGAAACACCTATTTACATTGGTTTCAGCAGAGGCCAGGCCAATCTCCAAGGCTCCTGATCTACACAGTTTCCAACCGATTT       180
        ----+----+----+----+----+----+----+----+----+----+----+----+----+----+----+----+----+----+
GTGTCTTTACCTTTGTGGATAAATGTAACCAAAGTCGTCTCCGGTCCGGTTAGAGGTTCCGAGGACTAGATGTGTCAAAGGTTGGCTAAA
 H  R  N  G  N  T  Y  L  H  W  F  Q  Q  R  P  G  Q  S  P  R  L  L  I  Y  T  V  S  N  R  F        55
     CDR1                                                                    CDR2

TCTGGGGTCCCAGACAGATTCAGCGGCAGTGGGTCAGGCACTGATTTCACACTGAAAATCAGCAGGGTGGAGGCTGAGGATGTTGGGGTT       270
        ----+----+----+----+----+----+----+----+----+----+----+----+----+----+----+----+----+----+
AGACCCCAGGGTCTGTCTAAGTCGCCGTCACCCAGTCCGTGACTAAAGTGTGACTTTTAGTCGTCCCACCTCCGACTCCTACAACCCCAA
 S  G  V  P  D  R  F  S  G  S  G  S  G  T  D  F  T  L  K  I  S  R  V  E  A  E  D  V  G  V        85

TATTTCTGCTCTCAAAGTTCACATGTTCCTCCCACGTTCGGTGCTGGGACAACGACTGGGAGATCAAACGT                         339
        ----+----+----+----+----+----+----+----+----+----+----+----+----+----+
ATAAAGACGAGAGTTTCAAGTGTACAAGGAGGGTGCAAGCCACGACCCTGTTGCTGACCCTCTAGTTTGCA
 Y  F  C  S  Q  S  S  H  V  P  P  T  F  G  A  G  T  R  L  E  I  K  R                            108
           CDR3
```

ANTHRACYCLINE-ANTIBODY CONJUGATES FOR CANCER THERAPY

RELATED APPLICATIONS

This application is a continuation-in-part of U.S. patent application Ser. No. 11/137,385 (now abandoned), filed May 26, 2005, which was a continuation of PCT/US04/01367, filed Jan. 20, 2004, which claimed the benefit under 35 U.S.C. 119(e) of Provisional U.S. Patent Application Ser. No. 60/442,125, filed Jan. 24, 2003. This application is also a continuation-in-part of U.S. patent application Ser. No. 11/754,902, filed May 29, 2007, which was a divisional of U.S. patent application Ser. No. 10/377,122 (now U.S. Pat. No. 7,312,318), filed Mar. 3, 2003, which claimed the benefit under 35 U.S.C. 119(e) of Provisional U.S. Patent Application Ser. No. 60/360,259, filed Mar. 1, 2002. The text of each priority application cited above is incorporated herein by reference in its entirety.

FIELD OF THE INVENTION

The invention relates to therapeutic conjugates with the ability to target various antigens. The conjugates contain a targeting moiety and a chemotherapeutic drug. In particular embodiments, the targeting moiety is an anti-CD74 antibody or antigen-binding fragment thereof and the chemotherapeutic drug is an anthracycline drug, such as doxorubicin or a derivative thereof. The targeting and the chemotherapeutic drug are linked via a linker comprising an intracellularly cleavable moiety.

BACKGROUND OF THE INVENTION

For many years it has been a goal of scientists in the field of specifically targeted drug therapy that antibodies could be used for the specific delivery of chemotherapy drugs to human cancers. Realization of such a goal could finally bring to cancer chemotherapy the concept of the magic bullet. A significant advance toward achieving this goal came with the advent of the hybridoma technique of Kohler and Milstein in 1975, and the subsequent ability to generate monoclonal antibodies (MAbs). During the past 25 years monoclonal antibodies have been raised against many antigenic targets that are over-expressed on cancerous cells. Either alone, or as conjugates of drugs, toxins, radionuclides or other therapy agents, many antibodies have been tested pre-clinically, and later in clinical trials.

Generally, antibodies by themselves, often termed "naked antibodies," have not been successful at making long-term survivorship the norm in patients with solid tumors, although survival advantages have lately been seen with antibody treatments directed against both breast and colon cancer (antibodies against HER2-neu and 17-1A, respectively). With hematological malignancies more success is being achieved with naked antibodies, notably against the B-cell lymphomas (antibodies against CD20 and CD22 on the surface of B-cells).

It appears self-evident, however, that the use of conjugates of tumor-associated antibodies and suitable toxic agents will be more efficacious than naked antibodies against most clinical cases of cancer. Here, an antibody also carries a toxic agent specifically to the diseased tissue, in addition to any toxicity it might inherently have by virtue of natural or re-engineered effector functions provided by the Fc portion of the antibody, such as complement fixation and ADCC (antibody dependent cell cytotoxicity), which set mechanisms into action that may result in cell lysis. However, it is possible that the Fc portion is not required for therapeutic function, as in the case of antibody fragments, other mechanisms, such as apoptosis, inhibiting angiogenesis, inhibiting metastatic activity, and/or affecting tumor cell adhesion, may come into play. The toxic agent is most commonly a chemotherapy drug, a particle-emitting radionuclide, or a bacterial or plant toxin. Each type of conjugate has its own particular advantages. Penetrating radionuclides and the bacterial and plant toxins are extremely toxic, usually orders of magnitude more toxic than standard chemotherapy drugs. This makes the former two useful with antibodies, since in a clinical situation the uptake of antibodies into diseased tissue is extremely low. The low antibody tumor uptake in clinical practice and the relatively low toxicity profile of cancer chemotherapy drugs, combined, is a major reason why antibody-drug conjugates have failed to live up to their promise, to date.

In preclinical animal xenograft models, set up to study human cancer, many antibody conjugates have been described which are able to completely regress or even cure animals of their tumors. However, tumor uptakes of antibody conjugates in many of these animal xenograft models are often in the 10-50% injected dose per gram of tissue range, whereas in the clinical situation, tumor uptakes in the 0.1-0.0001% injected dose per gram of tissue are more normal. It is no surprise, then, that antibody conjugates made with the more toxic radionuclides and toxins have generally fared somewhat better, clinically, than the corresponding antibody-drug conjugates with standard chemotherapeutic drugs. However, radionuclide antibody conjugates can often produce significant toxicity due to the presence of excess circulating, decaying radioactivity compared to tumor-localized activity. Toxin-antibody conjugates have suffered from the dual drawbacks of non-target tissue damage and immunoreactivity toward the plant or bacterial protein that is generally used. Whereas antibodies can now be made in human or in humanized (complementarity-determining region-grafted) forms, de-immunization of the toxin part of any conjugate will likely remain a significant obstacle to progress.

Despite the lack of efficacy in a clinical setting seen to date, antibody-drug conjugates still have compelling theoretical advantages. The drug itself is structurally well defined, not present in isoforms, and can be linked to the antibody protein using very well defined conjugation chemistries, often at specific sites remote from the antibodies' antigen binding regions. MAb-drug conjugates can be made more reproducibly than chemical conjugates involving antibodies and toxins, and, as such, are more amenable to commercial development and regulatory approval. For such reasons, interest in drug conjugates of antibodies has continued despite the disappointments encountered. In some recent instances, however, preclinical results have been quite promising. With continuing refinements in conjugation chemistries, and the ability to remove or reduce immunogenic properties of the antibody, the elusive promise of useful antibody-drug conjugates for clinical cancer therapy are being newly considered.

Relevant early work on antibody-drug conjugates found during in vitro and in vivo preclinical testing that the chemical linkages used often resulted in the loss of a drug's potency. Thus, it was realized many years ago that a drug would ideally need to be released in its original form, once internalized by a target cell by the antibody component, in order to be a useful therapeutic. Work during the 1980s and early 1990s then focused largely on the nature of the chemical linker between the drug and the antibody. Notably, conjugates prepared using mild acid-cleavable linkers were developed, based on the observation that pH inside tumors was often lower than normal physiological pH (U.S. Pat. Nos. 4,542,225; 4,569,789;

4,618,492; and 4,952,394). This approach culminated in a landmark paper by Trail et al. (Science 261:212-215 (1993)) showing that antibody-doxorubicin (DOX) conjugates, prepared with appropriate linkers, could be used to cure mice bearing a variety of human tumor xenografts, in preclinical studies.

This result was achieved with an antibody (termed BR96) that had a very large number of receptors on the tumor cells being targeted and the antibody-drug conjugate was highly substituted (6-8 DOX residues per unit of antibody). However, the conjugate was given in massive doses on a repeat basis in order to achieve efficacy. A need exists for drug-antibody conjugates that are efficacious at much lower dosages.

In the clinical situation, tumor uptake of antibodies would be much lower, and it has been suggested that more toxic drugs are needed to achieve a desirable therapeutic effect. More toxic drugs were used in the development of several distinct antibody-drug conjugates (U.S. Pat. Nos. 5,208,020; 5,416,064; 5,877,296; and 6,015,562). These efforts use drugs, such as derivatives of maytansinoids and calicheamicin, which are essentially too toxic to be used in standard chemotherapy. Conjugation to an antibody enables relatively more of the drug to be targeted to a tumor in relation to the often non-specific cell and protein binding seen with chemotherapy alone. The exquisite toxicity of drugs such as these might overcome the low levels of tumor-targeted antibody seen clinically, due to the low level of antigen binding sites generally seen on tumor targets. In preclinical studies, cures of mice bearing human tumor xenografts were seen at much lower doses of antibody-drug conjugate, than seen previously with antibody-drug conjugates using standard drugs, such as DOX (Liu et al., Proc. Natl. Acad. Sci. USA 93:8616-8623 (1996) and Hinman et al., Cancer Res. 53:3336-3342 (1993)). In the case of the maytansinoid-antibody conjugates (Liu), the amount of conjugate needed for therapy was over >50-fold less than needed previously with DOX conjugates (Trail, supra).

During development of these conjugates the linker between drug and antibody was thought to be critical for retention of good anti-tumor activity both in vitro and in vivo. The cited conjugates were made with an intracellularly-cleavable moiety (hydrazone) and a reductively labile (disulfide) bond between the drug and the antibody. While the hydrazone bond is apparently stable to in vivo serum conditions, normal disulfide bonds were found to be not stable enough for practical use. Conjugates were made that replaced a standard disulfide linkage with a hindered (geminal dimethyl) disulfide linkage in the case of the calicheamicins, or a methyl disulfide in the case of the maytansinoids. While this work was being done, separate work also continued on newer anthracycline-substituted antibody conjugates. In the case of newer DOX conjugated antibodies, it was found that superior results could be obtained by incorporating just a hydrazone as a cleavable unit, and attaching DOX to antibody via a thioether group, instead of a disulfide (U.S. Pat. No. 5,708,146). When linked in such a manner, and also using a branched linker capable of doubling the number of DOX units per MAb substitution site, an approximate order of magnitude increase in the efficacy of the new DOX-MAb conjugates was obtained (King et al., Bioconjugate Chem. 10:279-288, (1999)).

SUMMARY OF THE INVENTION

The present invention is directed to internalizing antibody conjugates of anthracycline drugs, particularly conjugates of anti-CD74 antibodies, such as the hLL1 antibody. Specific embodiments are exemplified by conjugates of doxorubicin (DOX), epirubicin, morpholinodoxorubicin (morpholino-DOX), cyanomorpholino-doxorubicin (cyanomorpholino-DOX), and 2-pyrrolino-doxorubicin (2-PDOX). 2-PDOX is particularly toxic, incorporating an enamine in its structure, which can act not only as an intercalator and topoisomerase inhibitor, but also as an alkylating agent having increased toxicity. Like DOX, 2-PDOX has relatively good aqueous solubility which means that it can be coupled to antibodies in multiply substituted amounts without precipitation of the antibody. The drugs described in detail below are consistently substituted at an average of 8 (typically measured at 7-9) drug moieties per molecule of antibody. The number of drugs, however, may also range between 6 to 10 molecules per molecule of antibody.

In one aspect, the invention relates to an immunoconjugate comprising a targeting moiety, an anthracycline drug and a linker binding the targeting moiety via a thiol group and the anthracycline chemotherapeutic drug via an intracellularly-cleavable moiety.

In a preferred embodiment, the targeting moiety is an antibody, such as an anti-CD74 MAb or antigen-binding fragment thereof, the anthracycline chemotherapeutic drug is DOX, 2-PDOX, morpholino-DOX or morpholinocyano-DOX, and the intracellularly-cleavable moiety is a hydrazone. In yet another preferred embodiment, the linker is a 4-[N-maleimidomethyl]cyclohexane-1-carboxylhydrazide radical.

In another aspect, the invention relates to an immunoconjugate comprising a disease-targeting antibody and an anthracycline chemotherapeutic drug. Many hundreds of examples of anthracycline drugs have been synthesized over the last 30-40 years or so, and they are discussed in detail elsewhere (see: Anthracycline Antibiotics; New Analogs, methods of Delivery, and Mechanisms of Action, Waldemar Priebe, Editor, ACS Symposium Series 574, American Chemical Society, Washington D.C., 1994). Such analogs are envisaged as within the scope of the current invention.

In a preferred embodiment, the invention relates to an immunoconjugate comprising a disease-targeting antibody and an anthracycline chemotherapeutic drug of the formula I or II:

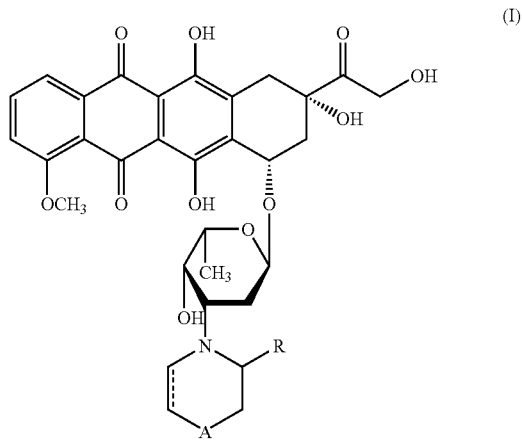

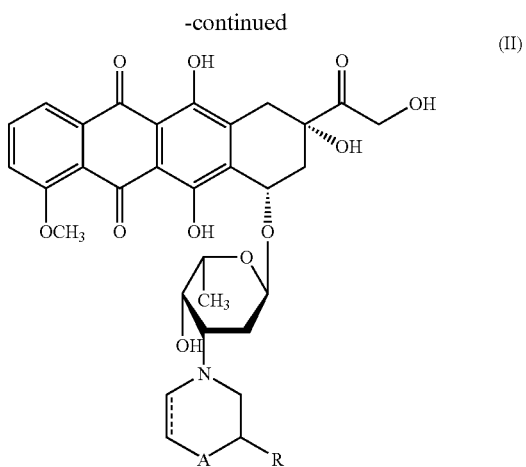

(II)

wherein, A is nothing or it may be selected from the group consisting of NH, N-alkyl, N-cycloalkyl, O, S, and $CH_2$; the dotted line denotes a single or a double bond; and R is H or CN; and a linker binding the targeting moiety via a sulfide group and the anthracycline chemotherapeutic drug via an intracellularly cleavable moiety. When A is "nothing," the carbon atoms adjacent to A, on each side, are connected by a single bond, thus giving a five-membered ring.

As used herein, "alkyl" refers to a saturated aliphatic hydrocarbon radical including straight chain and branched chain groups of 1 to 20 carbon atoms (whenever a numerical range; e.g. "1-20", is stated herein, it means that the group, in this case the alkyl group, may contain 1 carbon atom, 2 carbon atoms, 3 carbon atoms, etc. up to and including 20 carbon atoms). Alkyl groups containing from 1 to 4 carbon atoms are referred to as lower alkyl groups. More preferably, an alkyl group is a medium size alkyl having 1 to 10 carbon atoms e.g., methyl, ethyl, propyl, 2-propyl, n-butyl, iso-butyl, tert-butyl, pentyl, and the like. Most preferably, it is a lower alkyl having 1 to 4 carbon atoms e.g., methyl, ethyl, propyl, 2-propyl, n-butyl, iso-butyl, or tert-butyl, and the like.

As used herein "cycloalkyl" refers to a 3 to 8 member all-carbon monocyclic ring, an all-carbon 5-member/6-member or 6-member/6-member fused bicyclic ring or a multicyclic fused ring (a "fused" ring system means that each ring in the system shares an adjacent pair of carbon atoms with each other ring in the system) group wherein one or more of the rings may contain one or more double bonds but none of the rings has a completely conjugated pi-electron system. Examples, without limitation, of cycloalkyl groups are cyclopropane, cyclobutane, cyclopentane, cyclopentene, cyclohexane, cyclohexadiene, adamantane, cycloheptane, cycloheptatriene, and the like. A cycloalkyl group may be substituted or unsubstituted.

In another preferred embodiment, the intracellularly cleavable moiety is a hydrazone.

In a preferred embodiment, the antibody targets tumor-associated antigens, such as CD74. Tumor-associated antigens are defined as antigens expressed by tumor cells, or their vasculature, in a higher amount than in normal cells. Tumor-associated antigens may also be antigens associated with different normal cells, such as lineage antigens in hematopoietic cells, B-cells, T-cells or myeloid cells, whereby a patient can survive with a transient, selective decrease of said normal cells, while the malignant cells expressing the same antigen(s) are sufficiently destroyed to relieve the patient of symptoms and also improve the patient's condition. The antibody may also be reactive with an antigen associated with hematologic malignancies In yet another embodiment, the antibody is selected from the group of B-cell, T-cell, myeloid-cell, and other hematopoietic cell-associated antigens, such as CD19, CD20, CD21, CD22, CD23 in B-cells; CD33, CD45, and CD66 in myeloid cells; IL-2 (TAC or CD25) in T-cells; MUC1, tenascin, CD74, HLA-DR, CD80 in diverse hematopoietic tumor types; CEA, CSAp, MUC1, MUC2, MUC3, MUC4, PAM4, EGP-1, EGP-2, AFP, HCG, HER2/neu, EGFR, VEGF, P1GF, Le(y), carbonic anhydrase IX, PAP, PSMA, MAGE, S100, tenascin, and TAG-72 in various carcinomas, tenascin in gliomas, and antigens expressed by the vasculature and endothelial cells, as well as the supportive stroma, of certain tumors. In still another preferred embodiment, the antibody is selected from the group consisting of LL1 (anti-CD74), LL2 (anti-CD22), hA20 and rituximab (anti-CD20), M195 (anti-CD33), RS7 (anti-epithelial glycoprotein-1 (EGP-1)), 17-1A (anti-EGP-2), PAM-4, BrE3, and KC4, MN-14 (anti-carcinoembryonic antigen (CEA)), Mu-9 (anti-colon-specific antigen-p), Immu 31 (an anti-alpha-fetoprotein), anti-TAG-72 (e.g., CC49), anti-Tn, J591 (anti-PSMA), BC-2 (an anti-tenascin antibody) and G250 (an anti-carbonic anhydrase IX antibody). Other useful antigens that may be targeted using these conjugates include HER-2/neu, CD19, CD20 (e.g., C2B8, hA20, cA20, 1F5 Mabs) CD21, CD23, CD33, CD40, CD80, alpha-fetoprotein (AFP), VEGF, EGF receptor, P1GF (placenta growth factor), ILGF-1 (insulin-like growth factor-1), MUC1, MUC2, MUC3, MUC4, PSMA, gangliosides, HCG, EGP-2 (e.g., 17-1A), CD37, HLA-DR, CD30, Ia, Ii, A3, A33, Ep-CAM, KS-1, Le(y), 5100, PSA, tenascin, folate receptor, Thomas-Friedenreich antigens, tumor necrosis antigens, tumor angiogenesis antigens, Ga 733, IL-2 (CD25), T101, MAGE, CD66, CEA, NCA95, NCA90 or a combination thereof. Antibodies against TAAs may include, but are not limited to hPAM4 (U.S. Pat. No. 7,282,567), hA20 (U.S. Pat. No. 7,251,164), hA19 (U.S. Pat. No. 7,109,304), anti-AFP (U.S. Pat. No. 7,300,655), hLL1 (U.S. Pat. No. 7,312,318), hLL2 (U.S. Pat. No. 7,074,403), hMu-9 (U.S. Pat. No. 7,387, 773), hL243 (U.S. patent application Ser. No. 11/368,296), hMN-14 (U.S. Pat. No. 6,676,924), hMN-15 (U.S. patent application Ser. No. 10/672,278), hRS7 (U.S. Pat. No. 7,238, 785), the Examples section of each of which is incorporated herein by reference.

In a more preferred embodiment, the targeting antibody is directed against a surface antigen which is then rapidly internalized with the antibody. In an especially preferred embodiment the targeting antibody is directed against the CD74 antigen. Most preferably, the antibody is a chimeric, humanized or human monoclonal antibody comprising the CDR sequences of a murine LL1 anti-CD74 antibody, comprising light chain CDR1 (RSSQSLVHRNGNTYLH, SEQ ID NO:1), CDR2 (TVSNRFS, SEQ ID NO:2) and CDR3 (SQSSHVPPT, SEQ ID NO:3) and heavy chain CDR1 (NYGVN, SEQ ID NO:4), CDR2 (WINPNTGEPTFD-DDFKG, SEQ ID NO:5), and CDR3 (SRGKNEAWFAY, SEQ ID NO:6).

Also described are processes for the preparation of the compositions of the invention, together with methods of use of the said compositions. Preferably, the method comprises administering an anthracycline-anti-CD74 antibody conjugate to an individual with a cancer that expresses the CD74 antigen.

BRIEF DESCRIPTION OF THE DRAWINGS

FIG. 6 shows the alignment of the amino acid sequences of light and heavy chain variable regions of a human antibody, cLL1 and hLL1. FIG. 6A shows the VH amino acid sequence alignment of the human antibody RF-TS3, (SEQ ID NO:7) cLL1 (SEQ ID NO:8) and hLL1 (SEQ ID NO:9) and FIG. 6B shows the Vk amino acid sequence alignment of the human antibody HF-21/28, (SEQ ID NO:10) cLL1 (SEQ ID NO:11) and hLL1 (SEQ ID NO:12). Dots indicate the residues in cLL1 that are identical to the corresponding residues in the human antibodies. Boxed regions represent the CDR regions. Both N- and C-terminal residues (underlined) of cLL1 are fixed by the staging vectors used and not compared with the human antibodies. Kabat's Ig molecule number scheme is used.

FIG. 7 shows the DNA and amino acid sequences of the humanized LL1 (hLL1) heavy and light chain variable regions expressed in Sp2/0 cells. FIG. 7A shows the DNA (SEQ ID NO:13) and amino acid (SEQ ID NO:14) sequences of the hLL1VH and FIG. 7B shows the DNA (SEQ ID NO:15) and amino acid (SEQ ID NO:16) sequences of the hLL1Vk. Amino acid sequences encoded by the corresponding DNA sequences are given as one letter codes. The amino acid residues in the CDR regions are shown in bold and underlined. Kabat's Ig molecule numbering scheme is used for amino acid residues.

FIG. 10A shows the fate of the bound Ab followed for up to 3 days. FIG. 10B shows the result of hLL1 processing studied at early time points (less than 3 h). The data was averaged of two experiments.

DETAILED DESCRIPTION OF THE PREFERRED EMBODIMENTS

Figure 1:
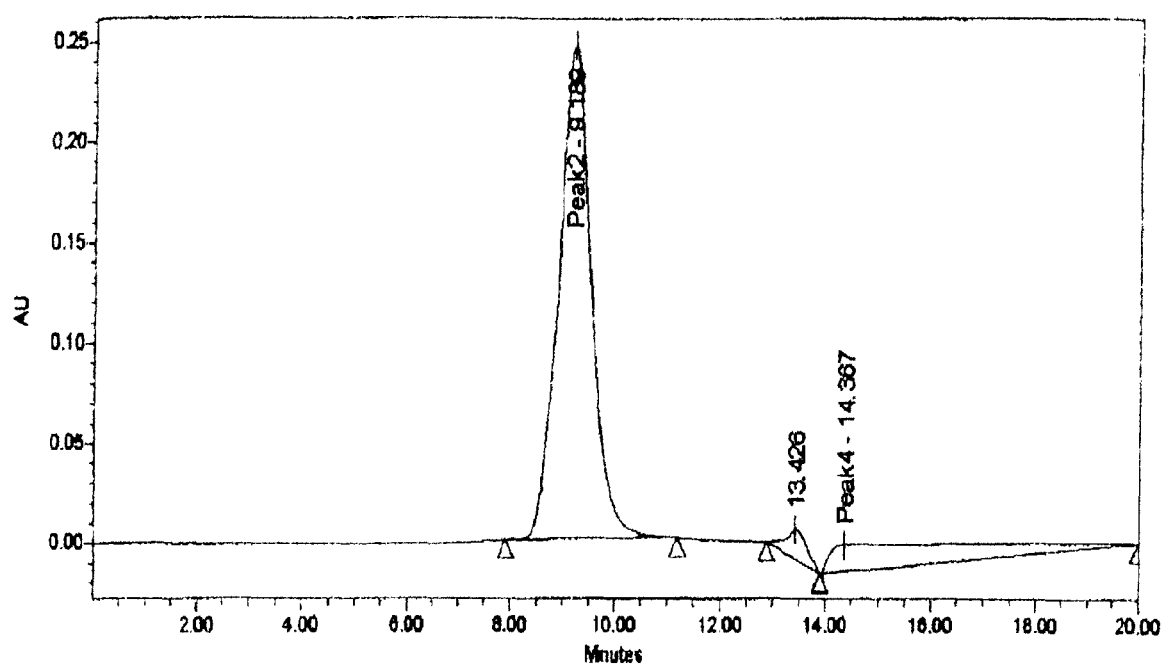
FIG. 1 is a representative size-exclusion HPLC trace of an anthracycline-antibody conjugate prepared using the methods described.

As used herein, "a" or "an" means "one or more" unless otherwise specified.

A "therapeutic agent" is a molecule or atom which is administered separately, concurrently or sequentially with an antibody moiety or conjugated to an antibody moiety, i.e., antibody or antibody fragment, or a subfragment, and is useful in the treatment of a disease. Examples of therapeutic agents include antibodies, antibody fragments, drugs, toxins, enzymes, nucleases, hormones, immunomodulators, antisense oligonucleotides, chelators, boron compounds, photoactive agents or dyes and radioisotopes.

INTRODUCTION

Chemotherapeutic drugs can be coupled to antibodies by several methods to form a antibody-drug conjugate. For example, the chemotherapeutic drugs may be attached to the antibody, or fragments thereof, after reduction of the antibody inter-chain disulfide bonds. This approach generates an average of eight-to-ten (depending on IgG type) free thiol groups per molecule of antibody, and does so in a reproducible manner at the limiting levels of thiol used in the reduction reaction. This method of attachment of the chemotherapeutic drugs is advantageous for the following reasons: first, the attached chemotherapeutic drugs are placed in an internal or semi-internal site on the antibody, or fragments thereof, which is not exposed on hydrophilic lysine residues. This serves to keep them more stable due to the more hydrophobic areas of the antibody, where the chemotherapeutic drugs are placed. Second, such a site does not alter the overall charge of the antibody, or fragments thereof. Third, placement on internal thiols is less likely to interfere in the ADCC and complement actions that are particularly important when naked versions of the antibody are used. Thus, the attachment site is chosen to be non-interfering, such that ADCC and complement fixation can be complementary to the antibodies, or the antibody fragments, role as a drug delivery vehicle. Fourth, placement at the internal thiol positions is less likely to lead to an immune response to the chemotherapeutic drugs, compared to placement of a multitude of chemotherapeutic drugs molecules on exposed lysine groups. In some embodiments, the overall electric charge of the antibody in the Ab-drug conjugate is not changed as compared to the charge of the antibody prior to the coupling. This is because no lysine residues are used in the conjugation reaction, and therefore no free, positive amino groups are modified to form, for example, neutral amide bonds.

Antibodies

An antibody as described herein, refers to a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment.

An antibody fragment is a portion of an antibody such as F(ab')$_2$, F(ab)$_2$, Fab', Fab, Fv, scFv (single chain Fv) and the like. Regardless of structure, an antibody fragment binds with the same antigen that is recognized by the intact antibody and is therefore an antigen-binding fragment of the antibody of which it is a portion. For example, antibody fragments include isolated fragments consisting of the variable regions, such as the "Fv" fragments consisting of the variable regions of the heavy and light chains, recombinant single chain polypeptide molecules in which light and heavy variable regions are connected by a peptide linker ("scFv proteins"). The Fv fragments may be constructed in different ways as to yield multivalent and/or multispecific binding forms.

As used herein, the term antibody fusion protein is a recombinantly-produced antigen-binding molecule in which two or more of the same or different natural antibody, single-chain antibody or antibody fragment segments with the same or different specificities are linked. A fusion protein comprises at least one specific binding site. Valency of the fusion protein indicates the total number of binding arms or sites the fusion protein has to antigen(s) or epitope(s); i.e., monovalent, bivalent, trivalent or multivalent. The multivalency of the antibody fusion protein means that it can take advantage of multiple interactions in binding to an antigen, thus increasing the avidity of binding to the antigen, or to different antigens. Specificity indicates how many different types of antigen or epitope an antibody fusion protein is able to bind; i.e., monospecific, bispecific, trispecific, multispecific. Using these definitions, a natural antibody, e.g., an IgG, is bivalent because it has two binding arms but is monospecific because it binds to one type of antigen or epitope. A monospecific, multivalent fusion protein has more than one binding site for the same antigen or epitope. For example, a monospecific diabody is a fusion protein with two binding sites reactive with the same antigen. The fusion protein may comprise a multivalent or multispecific combination of different antibody components or multiple copies of the same antibody component.

In a preferred embodiment, monoclonal antibodies are used that recognize or bind to markers or tumor-associated antigens that are expressed at high levels on target cells and that are expressed predominantly or only on diseased cells versus normal tissues, and antibodies that internalize rapidly. Antibodies useful within the scope of the claimed methods and compositions include antibodies against tumor-associated antigens, such as antibodies with properties as described above (and show distinguishing properties of different levels of internalization into cells and microorganisms), and contemplate the use of, but are not limited to, in cancer, the following antibodies: LL1 (anti-CD74), LL2 (anti-CD22), M195 (anti-CD33), MN-3 (anti-NCA90), RS7 (anti-epithelial glycoprotein-1 (EGP-1)), PAM-4, BrE3 and KC4 (all anti-MUC1), MN-14 (anti-carcinoembryonic antigen), Mu-9 (anti-colon-specific antigen-p), Immu 31 (an anti-alpha-fetoprotein), anti-TAG-72 (e.g., CC49), anti-Tn, J591 (anti-PSMA), M195 (anti-CD33) and G250 (an anti-carbonic anhydrase IX antibody). Other useful antigens and different epitopes of such antigens that may be targeted using these conjugates include HER-2/neu, CD19, CD20 (e.g., C2B8, hA20, 1F5 Mabs) CD21, CD23, CD25, CD30, CD33, CD37, CD40, CD74, CD80, alpha-fetoprotein (AFP), VEGF, EGF receptor, P1GF, MUC1, MUC2, MUC3, MUC4, PSMA, PAP, carbonic anhydrase IX, TAG-72, GD2, GD3, HCG, EGP-2 (e.g., 17-1A), HLA-DR, CD30, Ia, A3, A33, Ep-CAM, KS-1, Le(y), 5100, PSA, tenascin, folate receptor, Tn or Thomas-Friedenreich antigens, tumor necrosis antigens, tumor angiogenesis antigens, Ga 733, T101, MAGE, or a combination thereof. A number of the aforementioned antigens are disclosed in U.S. Provisional Application Ser. No. 60/426,379, entitled "Use of Multi-specific, Non-covalent Complexes for Targeted Delivery of Therapeutics," filed Nov. 15, 2002.

Antibodies of use may be commercially obtained from a wide variety of known sources. For example, a variety of antibody secreting hybridoma lines are available from the American Type Culture Collection (ATCC, Manassas, Va.). A large number of antibodies against various disease targets, including but not limited to tumor-associated antigens, have been deposited at the ATCC and/or have published variable region sequences and are available for use in the claimed methods and compositions. See, e.g., U.S. Pat. Nos. 7,312,318; 7,282,567; 7,151,164; 7,074,403; 7,060,802; 7,056,509; 7,049,060; 7,045,132; 7,041,803; 7,041,802; 7,041,293; 7,038,018; 7,037,498; 7,012,133; 7,001,598; 6,998,468; 6,994,976; 6,994,852; 6,989,241; 6,974,863; 6,965,018; 6,964,854; 6,962,981; 6,962,813; 6,956,107; 6,951,924; 6,949,244; 6,946,129; 6,943,020; 6,939,547; 6,921,645; 6,921,645; 6,921,533; 6,919,433; 6,919,078; 6,916,475; 6,905,681; 6,899,879; 6,893,625; 6,887,468; 6,887,466; 6,884,594; 6,881,405; 6,878,812; 6,875,580; 6,872,568; 6,867,006; 6,864,062; 6,861,511; 6,861,227; 6,861,226; 6,838,282; 6,835,549; 6,835,370; 6,824,780; 6,824,778; 6,812,206; 6,793,924; 6,783,758; 6,770,450; 6,767,711; 6,764,688; 6,764,681; 6,764,679; 6,743,898; 6,733,981; 6,730,307; 6,720,15; 6,716,966; 6,709,653; 6,693,176; 6,692,908; 6,689,607; 6,689,362; 6,689,355; 6,682,737; 6,682,736; 6,682,734; 6,673,344; 6,653,104; 6,652,852; 6,635,482; 6,630,144; 6,610,833; 6,610,294; 6,605,441; 6,605,279; 6,596,852; 6,592,868; 6,576,745; 6,572,856; 6,566,076; 6,562,618; 6,545,130; 6,544,749; 6,534,058; 6,528,625; 6,528,269; 6,521,227; 6,518,404; 6,511,665; 6,491,915; 6,488,930; 6,482,598; 6,482,408; 6,479,247; 6,468,531; 6,468,529; 6,465,173; 6,461,823; 6,458,356; 6,455,044; 6,455,040, 6,451,310; 6,444,206' 6,441,143; 6,432,404; 6,432,402; 6,419,928; 6,413,726; 6,406,694; 6,403,770; 6,403,091; 6,395,276; 6,395,274; 6,387,350; 6,383,759; 6,383,484; 6,376,654; 6,372,215; 6,359,126; 6,355,481; 6,355,444; 6,355,245; 6,355,244; 6,346,246; 6,344,198; 6,340,571; 6,340,459; 6,331,175; 6,306,393; 6,254,868; 6,187,287; 6,183,744; 6,129,914; 6,120,767; 6,096,289; 6,077,499; 5,922,302; 5,874,540; 5,814,440; 5,798,229; 5,789,554; 5,776,456; 5,736,119; 5,716,595; 5,677,136; 5,587,459; 5,443,953, 5,525,338. These are exemplary only and a wide variety of other antibodies and their hybridomas are known in the art. The skilled artisan will realize that antibody sequences or antibody-secreting hybridomas against almost any disease-associated antigen may be obtained by a simple search of the ATCC, NCBI and/or USPTO databases for antibodies against a selected disease-associated target of interest. The antigen binding domains of the cloned antibodies may be amplified, excised, ligated into an expression vector, transfected into an adapted host cell and used for protein production, using standard techniques well known in the art.

In another preferred embodiment, antibodies are used that internalize rapidly and are then re-expressed on cell surfaces, enabling continual uptake and accretion of circulating antibody-chemotherapeutic drug conjugate by the cell. In a preferred embodiment, the drug is anthracycline and the antibody-anthracycline conjugate is internalized into target cells and then the receptor is re-expressed on the cell surface. An example of a most-preferred antibody/antigen pair is LL1 and CD74 (invariant chain, class II-specific chaperone, Ii). The CD74 antigen is highly expressed on B cell lymphomas, certain T cell lymphomas, melanomas and certain other cancers (Ong et al., *Immunology* 98:296-302 (1999)).

In a preferred embodiment the antibodies that are used in the treatment of human disease are human or humanized (CDR-grafted into a human framework) versions of antibodies; although murine, chimeric and primatized versions of antibodies can be used. For veterinary uses, the same-species IgG would likely be the most effective vector, although cross-species IgGs would remain useful, such as use of murine antibodies in dogs (e.g., L243 anti-HLA-DR antibody for treating canine lymphoma). Same species immunoglobulin (IgG)s molecules as delivery agents are mostly preferred to minimize immune responses. This is particularly important when considering repeat treatments. For humans, a human or humanized IgG antibody is less likely to generate an anti-IgG immune response from patients. Suitable human antibody constant regions and/or hinge sequences may include IgG1, IgG2a, IgG3 or IgG4. Such human antibody constant region sequences may be incorporated into chimeric, humanized or human antibodies using techniques well known in the art. Targeting an internalizing antigen, antibodies such as hLL1 and hLL2 rapidly internalize after binding to target cells, which means that the conjugated chemotherapeutic drug is rapidly internalized into cells.

An immunomodulator, such as a cytokine can also be conjugated to the monoclonal antibody-anthracycline drug, or can be administered unconjugated to the chimeric, humanized or human monoclonal antibody-anthracycline drug conjugate of the preferred embodiments. The immunomodulator can be administered before, concurrently or after administration of the monoclonal antibody-anthracycline drug conjugate of the preferred embodiments. The immunomodulator can also be conjugated to a hybrid antibody consisting of one or more antibodies binding to different antigens. Such an antigen may also be an immunomodulator. For example, CD40 or other immunomodulators can be administered in combination with anti-CSAp or anti-CSAp/non-CSAp antibody combination either together, before or after the antibody combinations are administered. The monoclonal antibody-anthracycline drug conjugate can also be used in combination with, or conjugated to, as a fusion protein, such as against CD40.

As used herein, the term "immunomodulator" includes cytokines, stem cell growth factors, lymphotoxins, such as tumor necrosis factor (TNF), and hematopoietic factors, such as interleukins (e.g., interleukin-1 (IL-1), IL-2, IL-3, IL-6, IL-10, IL-12, IL-18, and IL-21), colony stimulating factors (e.g., granulocyte-colony stimulating factor (G-CSF) and granulocyte macrophage-colony stimulating factor (GM-CSF)), interferons (e.g., interferons-α, -β and -γ), the stem cell growth factor designated "S1 factor," erythropoietin and thrombopoietin. Examples of suitable immunomodulator moieties include IL-2, IL-6, IL-10, IL-12, IL-18, IL-21, interferon-γ, TNF-α, and the like.

An immunomodulator is a therapeutic agent that when present, alters, suppresses or stimulates the body's immune system. Typically, an immunomodulator of use stimulates immune cells to proliferate or become activated in an immune response cascade, such as macrophages, B-cells, and/or T-cells. An example of an immunomodulator as described herein is a cytokine, which is a soluble small protein of approximately 5-20 kDs that are released by one cell population (e.g., primed T-lymphocytes) on contact with specific antigens, and which act as intercellular mediators between cells. As the skilled artisan will understand, examples of cytokines include lymphokines, monokines, interleukins, and several related signaling molecules, such as tumor necrosis factor (TNF) and interferons. Chemokines are a subset of cytokines. Certain interleukins and interferons are examples of cytokines that stimulate T cell or other immune cell proliferation.

In a preferred embodiment, the immunomodulator enhances the effectiveness of the anthracycline drug-antibody conjugate, and in some instances by stimulator effector cells of the host.

Anti-CD74 Antibodies

Murine LL1 (mLL1 or murine anti-CD74 antibody) is a specific monoclonal antibody reactive with CD74, i.e., the invariant chain (Ii determinant) of the HLA-DR complex, on the surface of B-lymphocytes, monocytes and histiocytes, human B-lymphoma cell lines, melanomas, T-cell lymphomas and a variety of other tumor cell types (Hansen et al., *Biochem. J.* 320:293 (1996)). Cell surface-bound LL1 is rapidly internalized to the lysosomal compartment and quickly catabolized, much faster than other antibodies, such as anti-CD19 and anti-CD22. Id. This property of LL1 overcomes some of the aforementioned difficulties with immunotherapy. As discussed below, the administration of anthracycline-LL1 conjugates has demonstrated surprising efficacy against cancer cells at unexpectedly low dosages of conjugate. Because of the rapid internalization of the Ii chain, it is anticipated that other antibodies that bind to CD74 will exhibit the same surprising characteristics as LL1 with respect to efficacy of conjugated drugs, such as anthracyclines.

Murine LL1 was developed by fusion of mouse myeloma cells with splenocytes from BALB/c mice immunized with preparations from the Raji B-lymphoma cell line (called EPB-1 in Pawlak-Byczkowska et al., *Can. Res.*, 49: 4568 (1989)). The clinical use of mLL1, just as with most other promising murine antibodies, has been limited by the development in humans of a human anti-mouse antibody (HAMA) response. A HAMA response is generally not observed following injection of mLL1 Fab', as evidenced in a bone marrow imaging study using a mLL1 Fab' labeled with $^{99m}$Tc. Juweid et. al., *Nuc. Med. Comm.* 18: 142-148 (1997). However, in some therapeutic and diagnostic uses, a full-length anti-CD74 antibody may be preferred. The use of a full-length murine anti-CD74 antibody can limit the diagnostic and therapeutic usefulness of such antibodies and antibody conjugates, not only because of the potential anaphylactic problem, but also as a major portion of the circulating conjugate may be complexed to and sequestered by circulating anti-mouse antibodies. Although the use of antibody fragments of mLL1 may circumvent the problems of immunogenicity, there are circumstances in which whole IgG is more desirable and the induction of cellular immunity is intended for therapy or enhanced antibody survival time. In general, HAMA responses pose a potential obstacle to realizing the full diagnostic and therapeutic potential of murine anti-CD74 antibodies. Therefore, the development of chimeric, humanized and human anti-CD74 antibodies and fragments thereof, antibody fusion proteins, immunoconjugates, multivalent and/or multispecific antibodies, and vaccine conjugates thereof would be extremely useful for therapy and diagnosis, with reduced production of human anti-mouse antibodies.

The anti-CD74 antibodies disclosed herein may contain murine CDRs that have specificity for the CD74 antigen. The anti-CD74 antibodies may be humanized, chimeric or human antibodies. In preferred embodiments they contain the amino acids of the CDRs of a murine LL1 antibody, comprising light chain variable region CDR1 comprising an amino acid sequence RSSQSLVHRNGNTYLH (SEQ ID NO:1), CDR2 comprising an amino acid sequence TVSNRFS (SEQ ID NO:2), and CDR3 comprising an amino acid sequence SQSSHVPPT (SEQ ID NO:3) as well as heavy chain variable region CDR1 comprising an amino acid sequence NYGVN (SEQ ID NO:4), CDR2 comprising an amino acid sequence WINPNTGEPTFDDDFKG (SEQ ID NO:5), and CDR3 comprising an amino acid sequence SRGKNEAWFAY (SEQ ID NO:6). Further, the humanized, chimeric or human antibody retains substantially the specificity for CD74 of the parent murine antibody. Therefore such antibodies are of use to direct agents, such as therapeutic and/or diagnostic agents, to the MHC class-II invariant chain (Ii), present on the surface of cells, such as B-lymphocytes, monocytes histiocytes, B-cell lymphomas and leukemias, as well as myeloma cells, resulting in the rapid internalization of these antibodies and the conjugated agent(s).

As known in the art, a humanized anti-CD74 monoclonal antibody or fragment thereof may comprise the complementarity-determining regions (CDRs) of a murine anti-CD74 antibody, such as LL1, and the framework (FR) and constant regions of a human antibody. The human FRs of the light and heavy chain variable regions may be modified to maintain specificity and affinity for CD74 by substituting at least one amino acid substituted from the corresponding FRs of the parent murine antibody. More specifically, one or more amino acids from the LL1 murine antibody identified by amino acid residues 2, 3, 4, 46, 87 and 100 of the murine light chain variable region of the cLL1Vk sequence of FIG. 6B, and amino acid residues 5, 37, 38, 46, 68, 91 and 93 of the murine heavy chain variable region of the cLL1VH sequence of FIG. 6A may be maintained in the human FRs of the humanized LL1 (hLL1) antibody.

In a preferred embodiment, the humanized LL1 (hLL1) or fragment thereof that contains a heavy chain variable region sequence as shown in FIG. 7A and a light chain variable region shown in FIG. 7B is used in the methods disclosed herein. The humanized anti-CD74 antibody or fragment thereof may also contain light and heavy chain constant region of a human antibody or a portion thereof, such as a human IgG1 antibody.

Although humanized anti-CD74 antibodies are preferred, chimeric anti-CD74 (cCD74) antibodies or fragments thereof also are encompassed. In one embodiment, the chimeric anti-CD74 monoclonal antibody, or fragment thereof comprises the light and heavy chain CDRs of a murine LL1 antibody as well as murine LL1 FR variable region sequences (FIG. 6). In a further embodiment the chimeric anti-CD74 antibody comprises the light and heavy chain constant regions of a human antibody.

Also encompassed is a human anti-CD74 monoclonal antibody or fragment thereof comprising light chain variable region CDR1 comprising an amino acid sequence RSSQSLVHRNGNTYLH (SEQ ID NO:1), CDR2 comprising an amino acid sequence TVSNRFS (SEQ ID NO:2), and CDR3 comprising an amino acid sequence SQSSHVPPT (SEQ ID NO:3) as well as heavy chain variable region CDR1 comprising an amino acid sequence NYGVN (SEQ ID NO:4), CDR2 comprising an amino acid sequence WINPNTGEPTFDDDFKG (SEQ ID NO:5), and CDR3 comprising an amino acid sequence SRGKNEAWFAY (SEQ ID NO:6). The human anti-CD74 antibody will also contain human antibody FR and constant region sequences.

Each of the human, chimeric or humanized anti-CD74 antibody is preferably an IgG1, where the constant regions are preferably a human IgG1, but the IgG1 may be referred to as a human IgG1, a chimeric IgG1 or a humanized IgG1, respectively. In particular, the humanized CD74 antibody, hLL1, has constant domains and the hinge region from a human IgG1. Preferably, both the chimeric and the human LL1 antibody has the same constant domain and hinge region. However, modifications can be made so that the constant regions of the IgG1 are replaced with human constant regions of human IgG2a, IgG3 or IgG4.

Also encompassed is a murine anti-CD74 monoclonal antibody or fragment thereof, comprising CDRs of a light chain variable region of a murine anti-CD74 antibody, that comprises CDR1 comprising an amino acid sequence RSSQSLVHRNGNTYLH (SEQ ID NO:1), CDR2 comprising an amino acid sequence TVSNRFS (SEQ ID NO:2), and CDR3 comprising an amino acid sequence SQSSHVPPT (SEQ ID NO:3). Further, the murine anti-CD74 monoclonal antibody or fragment thereof, comprising CDRs of a heavy chain variable region of a murine anti-CD74 antibody, that comprises CDR1 comprising an amino acid sequence NYGVN (SEQ ID NO:4), CDR2 comprising an amino acid sequence WINPNTGEPTFDDDFKG (SEQ ID NO:5), and CDR3 comprising an amino acid sequence SRGKNEAWFAY (SEQ ID NO:6). More preferably, the murine anti-CD74 monoclonal antibody or fragment thereof comprising complementarity-determining regions (CDRs) of murine anti-CD74 (mLL1) and the framework (FR) regions of a murine anti-CD74 antibody, wherein the light chain variable region of said murine antibody comprises CDR1 comprising an amino acid sequence RSSQSLVHRNGNTYLH (SEQ ID NO:1), CDR2 comprising an amino acid sequence TVSNRFS (SEQ ID NO:2), and CDR3 comprising an amino acid sequence SQSSHVPPT (SEQ ID NO:3), and wherein the heavy chain variable region of said murine antibody comprises CDR1 comprising an amino acid sequence NYGVN (SEQ ID NO:4), CDR2 comprising an amino acid sequence WINPNTGEPTFDDDFKG (SEQ ID NO:5), and CDR3 comprising an amino acid sequence SRGKNEAWFAY (SEQ ID NO:6).

Each of the human, chimeric, humanized or murine anti-CD74 antibodies or fragment thereof possess at least one of the following properties: it binds specifically and is reactive with CD74, its binding to CD74 is blocked by an antibody or fragment thereof specific for or reactive with CD74; it is internalized by Raji lymphoma cells in culture; and it induces apoptosis of Raji cells in cell culture when cross-linked with goat antisera reactive with the Fc of a murine IgG1 antibody.

The fragments of the human, chimeric or humanized anti-CD74 antibody may be a F(ab')$_2$, Fab, scFv, Fv, or a fusion construct utilizing part or all the light and heavy chains of the F(ab')$_2$, Fab, scFv or Fv fragments, as long as the fragment binds to CD74.

Methods of Antibody Production

The VK and VH sequences for the chimeric or humanized anti-CD74 antibody can amplified by PCR as described by Orlandi et al., (Proc. Natl. Acad. Sci., USA, 86: 3833 (1989)). VK sequences may be amplified using the primers CK3BH and VK5-3 (Leung et al., BioTechniques, 15: 286 (1993)), while VH sequences can be amplified using the primer CH$_1$B which anneals to the CH1 region of murine IgG, and VHI-BACK (Orlandi et al., 1989 above). The PCR reaction mixtures containing 10 µl of the first strand cDNA product, 9 µl of 10×PCR buffer [500 mM KCl, 100 mM Tris-HCl (pH 8.3), 15 mM MgCl$_2$, and 0.01% (w/v) gelatin] (Perkin Elmer Cetus, Norwalk, Conn.), can be subjected to 30 cycles of PCR. Each PCR cycle preferably consists of denaturation at 94° C. for 1 min, annealing at 50° C. for 1.5 min, and polymerization at 72° C. for 1.5 min. Amplified VK and VH fragments can be purified on 2% agarose (BioRad, Richmond, Calif.). Oligonucleotides may be synthesized using commercially available synthesizers by standard techniques or may alternatively be purchased from known commercial sources.

PCR products for VK can be subcloned into a staging vector, such as a pBR327-based staging vector VKpBR that contains an Ig promoter, a signal peptide sequence and convenient restriction sites to facilitate in-frame ligation of the VK PCR products. PCR products for VH can be subcloned into a similar staging vector, such as the pBluescript-based VHpBS. Individual clones containing the respective PCR products may be sequenced by, for example, the method of Sanger et al., *Proc. Natl. Acad. Sci., USA,* 74: 5463 (1977).

The plasmids encoding heavy and light chains can be co-transfected into an appropriate cell, e.g., myeloma Sp2/0 or variants thereof, such as Sp-EEE containing a triple mutant Bcl-2 gene (see, e.g., U.S. Pat. Nos. 7,531,327 and 7,537,930, the Examples section of each incorporated herein by reference), colonies selected for hygromycin resistance, and supernatant fluids monitored for production of chimeric or humanized anti-CD74 antibodies by, for example, an ELISA assay, as described below.

Transfection, and assay for antibody secreting clones by ELISA, can be carried out as follows. About 10 µg of hLL1 pith (light chain expression vector) and 20 µg of hLL1pG1g (heavy chain expression vector) can be used for the transfection of 5×10$^6$ SP2/0 myeloma cells by electroporation (Bio-Rad, Richmond, Calif.) according to Co et al., J. Immunol., 148: 1149 (1992). Following transfection, cells may be grown in 96-well microtiter plates in complete HSFM medium (GIBCO, Gaithersburg, Md.) at 37° C., 5% CO$_2$. The selection process can be initiated after two days by the addition of hygromycin selection medium (Calbiochem, San Diego, Calif.) at a final concentration of 500 µg/ml of hygromycin. Colonies typically emerge 2-3 weeks post-electroporation. The cultures can then be expanded for further analysis.

Transfectoma clones that are positive for the secretion of chimeric or humanized heavy chain can be identified by ELISA assay. Briefly, supernatant samples (100 µl) from transfectoma cultures are added in triplicate to ELISA microtiter plates precoated with goat anti-human (GAH)-IgG, F(ab')$_2$ fragment-specific antibody (Jackson ImmunoResearch, West Grove, Pa.). Plates are incubated for 1 h at room temperature. Unbound proteins are removed by washing three times with wash buffer (PBS containing 0.05% polysorbate 20). Horseradish peroxidase (HRP) conjugated GAH-IgG, Fc fragment-specific antibodies (Jackson ImmunoResearch, West Grove, Pa.) are added to the wells, (100 µl of antibody stock diluted×10$^4$, supplemented with the unconjugated antibody to a final concentration of 1.0 µl/ml). Following an incubation of 1 h, the plates are washed, typically three times. A reaction solution, [100 µl, containing 167 µg of orthophenylene-diamine (OPD) (Sigma, St. Louis, Mo.), 0.025% hydrogen peroxide in PBS], is added to the wells. Color is allowed to develop in the dark for 30 minutes. The reaction is stopped by the addition of 50 µl of 4 N HCl solution into each well before measuring absorbance at 490 nm in an automated ELISA reader (Bio-Tek instruments, Winooski, Vt.). Bound chimeric antibodies are than determined relative to an irrelevant chimeric antibody standard (obtainable from Scotgen, Ltd., Edinburgh, Scotland).

Antibodies can be isolated from cell culture media as follows. Transfectoma cultures are adapted to serum-free medium. For production of chimeric antibody, cells are grown as a 500 ml culture in roller bottles using HSFM. Cultures are centrifuged and the supernatant filtered through a 0.2 micron membrane. The filtered medium is passed through a protein A column (1×3 cm) at a flow rate of 1 ml/min. The resin is then washed with about 10 column volumes of PBS and protein A-bound antibody is eluted from the column with 0.1 M glycine buffer (pH 3.5) containing 10 mM EDTA. Fractions of 1.0 ml are collected in tubes containing 10 µl of 3 M Tris (pH 8.6), and protein concentrations determined from the absorbency at 280/260 nm. Peak fractions are pooled, dialyzed against PBS, and the antibody concentrated, for example, with the Centricon 30 (Amicon, Beverly, Mass.). The antibody concentration is determined by ELISA, as before, and its concentration adjusted to about 1 mg/ml using PBS. Sodium azide, 0.01% (w/v), is conveniently added to the sample as preservative.

Antibody-Chemotherapeutic Drug Conjugates

In preferred embodiments, the claimed methods and compositions concern a conjugate of an anthracycline drug and an antibody, wherein the anthracycline drug and the antibody are linked via a linker comprising a hydrazide and a maleimide. The linker preferably is 4-(N-maleimidomethyl)cyclohexane-1-carboxyl hydrazide. The conjugate preferably has the formula:

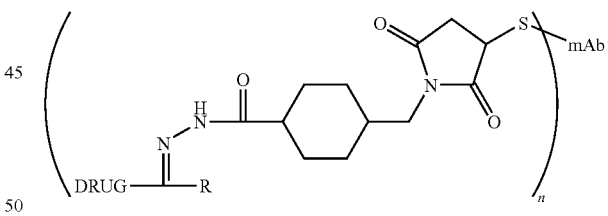

wherein n is 6 to 10.

Further, the antibody is directed against or recognizes a tumor-associated antigen. The antibody may be a monoclonal antibody, an antigen-binding fragment thereof or an antibody fusion protein. The antibody fusion protein may be multivalent and/or multispecific. The antibody fusion protein in the conjugate may comprise two or more of the same or different natural or synthetic antibody, single-chain antibody or antibody fragment segments with the same or different specificities. The antibody or antibody fragment of the fusion protein can be selected from the group consisting of LL1, LL2, M195, MN-3, RS7, 17-1A, RS11, PAM-4, KC4, BrE3, MN-14, Mu-9, Immu 31, CC49, Tn antibody, J591, Le(y) antibody and G250.

This tumor-associated antigen may be targeted by an internalizing antibody. The conjugate is useful for targeting carcinomas, sarcomas, lymphomas, leukemias, gliomas or skin cancers, such as melanomas. The tumor-associated antigen preferably is selected from the group consisting of CD74, CD22, EPG-1, CEA, colon-specific antigen-p mucin (CSAp), carbonic anhydrase IX, HER-2/neu, CD19, CD20, CD21, CD23, CD25, CD30, CD33, CD40, CD45, CD66, NCA90, NCA95, CD80, alpha-fetoprotein (AFP), VEGF, EGF receptor, P1GF, MUC1, MUC2, MUC3, MUC4, PSMA, GD2, GD3 gangliosides, HCG, EGP-2, CD37, HLA-D-DR, CD30, Ia, Ii, A3, A33, Ep-CAM, KS-1, Le(y), S100, PSA, tenascin, folate receptor, Tn and Thomas-Friedenreich antigens, tumor necrosis antigens, tumor angiogenesis antigens, Ga 733, IL-2, MAGE, and a combination thereof. More preferably the tumor-associated antigen is selected from the group consisting of CD74, CD19, CD20, CD22, CD33, EPG-1, MUC1, CEA and AFP. Most preferably, the antigen is CD74. These tumor-associated antigens may be lineage antigens (CDs) of B-cells, T-cells, myeloid cells, or antigens associated with hematologic malignancies.

The antibody portion of the conjugate can be murine, chimeric, primatized, humanized, or human. The antibody may be an intact immunoglobulin or an antigen-binding fragment thereof, such as an IgG or a fragment thereof. Preferably, the antibody is directed against B-cells, such as an antigen selected from the group consisting of CD19, CD20, CD21, CD22, CD23, CD30, CD37, CD40, CD74, CD80, and HLA-DR. The antibody, antigen-binding fragment thereof or fusion protein, preferably is selected from the group of LL1, LL2, L243, C2B8, A20, MN-3, M195, MN-14, anti-AFP, Mu-9, PAM-4, RS7, RS11 and 17-1A. More preferably, the antibody is LL1, LL2, L243, C2B8, or hA20. Most preferably, the antibody is LL1. Additionally, the antibody is linked to the drug via a linker which is attached to a reduced disulfide bond on the antibody, which may be an interchain disulfide bond on the antibody.

The anthracycline drug portion of the conjugate is preferably selected from the group consisting of daunorubicin, doxorubicin, epirubicin, 2-pyrrolinodoxorubicin, morpholino-doxorubicin, and cyanomorpholino-doxorubicin. Further, the anthracycline drug can be linked to the antibody through the 13-keto moiety. Preferably, there are 6-10 molecules of anthracycline drug per molecule of antibody. Additionally, the antibody-anthracycline conjugate is internalized into target cells, and the antigen is then re-expressed on the cell surface.

Further disclosed is a process for producing the conjugate described herein, wherein the linker is first conjugated to the anthracycline drug, thereby producing an anthracycline drug-linker conjugate, and wherein the anthracycline drug-linker conjugate is subsequently conjugated to a thiol-reduced monoclonal antibody or antibody fragment. The anthracycline drug-linker conjugate may be purified prior to conjugation to the thiol-reduced monoclonal antibody or antibody fragment but it is not necessary to do so. Thus, preferably there is no need to purify the anthracycline drug-linker conjugate prior to conjugation to the thiol-reduced monoclonal antibody or antibody fragment. The process for preparing the conjugate should be such that the secondary reactive functional groups on the anthracycline drug are not compromised. Additionally, the process for preparing the conjugate should not compromise the alkylating groups on the anthracycline drugs. The anthracycline drug in the conjugate preferably is 2-pyrrolino-doxorubicin-, morpholino-doxorubicin or cyanomorpholino-doxorubicin.

The chemotherapeutic drug molecules are separately activated for conjugation to the antibody such that they contain a free maleimide group, specific for thiol reaction at neutral pH. When the chemotherapeutic drug bears a reactive ketone, the ketone can be converted to hydrazone using the commercially available linker 4-[N-maleimidomethyl]cyclohexane-1-carboxylhydrazide $M_2C_2H$; Pierce Chemical Co., Rockford, Ill.) [also supplied as the trifluoroacetate salt by Molecular Biosciences, Inc., Boulder, Colo.] as shown in Scheme I, below.

In Scheme I, the DRUG is a chemotherapeutic drug, preferably an anthracycline drug and the R group is either a hydrogen atom or a $C_1$-$C_6$ alkyl group optionally substituted with a hydroxyl group (—OH).

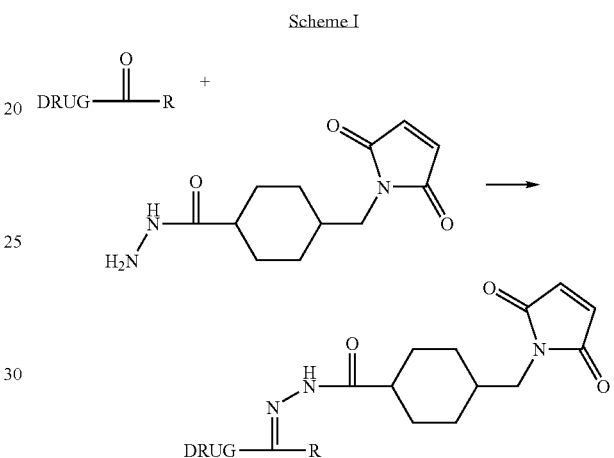

Scheme I

While not being bound by theory, the linker $M_2C_2H$ is thought to be a particularly useful linker in the context of the preferred embodiments for two reasons. First, the cyclohexyl group in the linker is thought to stabilize the hydrazone functionality. It is important that the hydrazone linkage used is substantially stable to serum conditions, and the cyclohexyl group proximal to the formed hydrazone results in a more stable hydrazone bond in comparison to a more standard straight-chain alkyl group. Second, the hydrazone produced from the reaction of the ketone with this carboxyl hydrazide is cleaved once the chemotherapeutic drug-antibody conjugate is internalized into the cell.

The maleimide-substituted chemotherapeutic drugs, in slight excess (1 to 5 fold molar) to available thiol groups on the reduced antibody are mixed in an aqueous solution with the reduced antibody. The reaction is performed at neutral, near-neutral or below neutral pH, preferably from about pH 4 to about pH 7. The components are allowed to react for a short reaction time of from about 5 to about 30 minutes. The skilled artisan would recognize, however, that the reaction conditions may be optimized with respect to reaction time and pH. The chemotherapeutic drug-antibody conjugate, shown schematically below (wherein n is an integer from 1 to 10, preferably from 1 to 8), is then separated from chemotherapeutic drug and other buffer components by chromatography through size-exclusion and hydrophobic interaction chromatography columns. In a preferred embodiment, the drug is an anthracycline and n is an integer from 6-10.

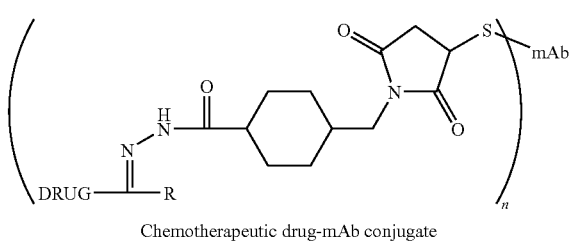

Chemotherapeutic drug-mAb conjugate

The above conditions are optimal in the case of 2-PDOX. The reaction conditions are optimal since they ensure that only the freely generated thiol groups of the antibody react with the maleimide-activated chemotherapeutic drug, while the enamine of 2-PDOX is not impinged by the reaction conditions. It is surprising that the thiol-maleimide coupling can be carried out in the presence of an alkylatable group, as exemplified here by the enamine group.

In a preferred embodiment, the chemotherapeutic drugs that are used are anthracycline drugs. These drugs comprise a large class of derivatives typified by one of the original members of the group, doxorubicin (DOX), and its isomer, epirubicin.

Both doxorubicin and epirubicin are widely used in cancer therapy. In another preferred embodiment the chemotherapeutic drugs include analogs of 2-PDOX, namely, morpholino- and cyanomorpholino-doxorubicin (morpholino-DOX and cyanomorpholino DOX, respectively). In another embodiment the chemotherapeutic drugs include daunorubicin.

The skilled artisan will recognize that the anthracycline drugs of the preferred embodiments contain a number of reactive groups, which may be referred to as secondary reactive functional groups, that may require protection with protective groups well known in the art. Prior to conjugation of the drug with the linker and/or prior to conjugation of the drug-linker conjugate and the antibody; protection may be necessary so as to not compromise the integrity of the reactive groups. See Greene and Wuts, Protective Groups in Organic Synthesis (John Wiley & Sons 2d ed. 1991. The reactive groups include the carbonyl groups in the anthraquinone core of the anthracycline drugs; groups which, under certain conditions, may be react with a nucleophile. Other reactive groups include the various alcohol groups that are located throughout the anthracycline drug molecules; groups, which under certain conditions may react with electrophiles. Lastly, other reactive groups include the amine group present in DOX and the enamine group in 2-PDOX; both of which may react with an electrophile. In the case of anthracycline drugs bearing an alkylating group (e.g., the enamine of 2-PDOX), it may be necessary to control the reaction conditions such that the integrity of the alkylating group is not compromised.

Within the anthracycline drug class, individual drugs, of toxicities varying over a 1-10,000 fold range (3-4 order-of-magnitude) range, can be interchanged on the basis of their varying toxicities, in order to generate more or less toxic immunoconjugates. Anthracyclines can exert their toxic effect on target cells by several mechanisms, including inhibition of DNA topoisomerase 2, intercalation into DNA, redox reactions and binding to certain intracellular or membrane proteins. Additionally, analogs can be designed that have additional mechanisms of cell killing, such as a potential to be alkylated. Exemplary analogs are anthracyclines bearing an alkylating moiety, as in the case of the 2-PDOX analog. In this instance, the alkylating moiety is an enamine group. In the 2-PDOX analog, the enamine group in the pyrrolino-ring is highly reactive to nucleophiles under physiologic conditions.

Pharmaceutical Compositions and Methods of Administrations

Certain embodiments relate to a pharmaceutical composition comprising the antibody-drug conjugate and a pharmaceutically acceptable carrier or excipient. By "pharmaceutically acceptable carrier" is intended, but not limited to, a non-toxic solid, semisolid or liquid filler, diluent, encapsulating material or formulation auxiliary of any type known to persons skilled in the art. Diluents, such as polyols, polyethylene glycol and dextrans, may be used to increase the biological half-life of the conjugate.

Certain embodiments are directed to a method for treating disease in a mammal comprising administering a conjugate of an antibody and an anthracycline drug as described herein. The present method also comprises administering the antibody-anthracycline conjugate described herein in all of its permutations preceded by, concomitantly with, or subsequent to other standard therapies, wherein said standard therapy is selected from the group consisting of radiotherapy, surgery and chemotherapy.

The instant claims are intended to encompass a method for treating disease in a mammal comprising administering two or more conjugates of an antibody and an anthracycline drug that target different antigens or different epitopes of the same antigen on the same diseased cells. Additionally encompassed is a method for treating disease in a mammal comprising administering a conjugate of an antibody and an anthracycline drug preceded by, concomitantly with, or subsequent to a second antibody-based treatment, such that the second antibody in the second antibody-based treatment targets a different antigen or a different epitope on the same antigen on diseased cells than the antibody in the conjugate.

In some embodiments, the antibody-drug conjugate alone or a pharmaceutical composition comprising the antibody-drug conjugate and a pharmaceutically acceptable carrier or excipient may be used in a method of treating a subject, comprising administering a therapeutically effective amount of the antibody-drug conjugate to a subject.

In preferred embodiments, the subject is a mammal. Exemplary mammals include human, pig, sheep, goat, horse, mouse, dog, cat, cow, etc. Diseases that may be treated with the antibody-drug conjugate include cancer, such as cancer of the skin, head and neck, lung, breast, prostate, ovaries, endometrium, cervix, colon, rectum, bladder, brain, stomach, pancreas or lymphatic system may be treated. Patients suffering from B- or T-cell cancer, non-Hodgkin's lymphoma, Hodgkin's disease, lymphatic or myeloid leukemias, multiple myeloma, sarcoma and melanoma may be treated by administration of a therapeutic amount of the antibody-drug conjugate of the present invention.

The antibody-drug conjugate may be administered intravenously, intra-peritoneally, intra-arterially, intra-thecally, intra-vesically, or intratumorally. The conjugate may be given as a bolus or as an infusion on a repeat and/or a cyclical basis. The infusion may be repeated for one or more times depending on the dose of drug and tolerability of the conjugate in terms of side effects and is determined by the managing physician. One of ordinary skill will appreciate that effective amounts of the antibody-drug conjugate can be determined empirically. The agents can be administered to a subject, in need of treatment of cancer, as pharmaceutical compositions in combination with one or more pharmaceutically acceptable excipients. It will be understood that, when administered to a human patient, the total daily usage of the agents or composition will be decided by the attending physician within the scope of sound medical judgment. The specific therapeutically effective dose level for any particular patient will depend upon a variety of factors: the type and degree of the cellular response to be achieved; activity of the specific antibody-drug conjugate or composition employed; the specific antibody-drug conjugate or composition employed; the age, body weight, general health, sex and diet of the patient; the time of administration, route of administration, and rate of excretion of the agent; the duration of the treatment; drugs used in combination or coincidental with the specific agent; and like factors well known in the medical arts. For example, it is well within the skill of the art to start doses of the agents at levels lower than those required to achieve the desired therapeutic effect and to-gradually increase the dosages until the desired effect is achieved.

In a preferred embodiment, the antibody-anthracycline conjugate is administered preceded by, concomitantly with, or subsequent to other standard therapies including radio-therapy, surgery or chemotherapy.

In another preferred embodiment, two or more conjugates of an antibody and an anthracycline drug are administered which conjugates target different antigens or different epitopes of the same antigen on the same diseased cells. In yet another preferred embodiment, a conjugate of an antibody and an anthracycline drug is administered, preceded by, concomitantly with, or subsequent to another antibody-based treatment. This additional antibody-based treatment may include the administration of two or more antibody-based treatments, to include naked therapy, where the antibody is administered alone or in combination with another therapeutic-agent that is administered either conjugated or unconjugated to the antibody. The conjugation may utilize the presently disclosed linker or another type linker. When two antibody-based treatments are administered, these treatment are such that whichever antibody is administered second targets a different antigen or a different epitope on the same antigen on diseased cells. The second antibody could also be conjugated with another (different) drug or with a therapeutic isotope, thus providing an antibody-based combination therapy. It is also appreciated that this therapy can be combined, with administration before, simultaneously, or after with cytokines that either enhance the antitumor effects or prevent or mitigate the myelosuppressive effects of the therapeutic conjugates.

Each of the above identified methods of treatment may additionally include the administration of one or more immunomodulators. These immunomodulators may be selected from the group consisting of interferons, cytokines, stem cell growth factors, colony-stimulating factors, lymphotoxins and other hematopoietic factors. The interferon is preferably α-interferon, β-interferon or γ-interferon and the hematopoietic factors may be selected from the group consisting of erythropoietin, thrombopoietin, interleukins (ILs), colony stimulating factors (CSF), granulocyte macrophage-colony stimulating factor (GM-CSF) and G-CSF. The interleukin may be selected from the group consisting of IL-1, IL-2, IL-3, IL-6, IL-10, IL-12, IL-18, and IL-21. The immunomodulator or hematopoietic factor may administered before, during, or after immunoconjugate therapy. The immunomodulator is administered to enhance the effectiveness of the administered conjugate of the present invention.

Kits

The preferred embodiments also contemplate kits comprising a conjugate of a monoclonal antibody and an anthracycline drug in a suitable container. The conjugate preferably includes a linker comprising a hydrazide and a maleimide. The monoclonal antibody-anthracycline drug conjugate is provided in a sterile container in liquid, frozen or lyophilized form. The monoclonal antibody-anthracycline drug conjugate can be diluted or reconstituted prior to administration to a patient in need thereof.

In a further embodiment, the conjugate of an anthracycline drug and an antibody, wherein the anthracycline drug and the antibody are linked via a linker comprising a hydrazide and a maleimide and wherein at least one immunomodulator is further conjugated to the antibody. The conjugate can then be administered to patients in need of therapy as described herein for the conjugate alone or in combination other therapies.

The present invention is illustrated by the following examples, without limiting the scope of the invention.

EXAMPLES

General 2-pyrrolino-doxorubicin was prepared using a modified method, based on the original description of Nagy et al. (Proc. Natl. Acad. Sci, U.S.A. 93:2464-2469 (1996)). Morpholino-DOX and cyanomorpholino-DOX were both synthesized from doxorubicin using published methods (Acton et al., J. Med. Chem. 27:638-645 (1984)).

Example 1

Synthesis of 2-PDOX

Synthesis of 2-pyrrolino-doxorubicin (2-PDOX): 4-iodobutyraldehyde: 2-(3-chloropropyl)-1,3-dioxolane (1.3 mL; 10 mM) was dissolved in 200 mL of acetone containing 30 g of sodium iodide (200 mmol; 20-fold excess). The solution is refluxed for 24 h and then evaporated to dryness. The crude mixture is used in the next reaction. Doxorubicin hydrochloride (550 mg, 946 μmol) is dissolved in 6.5 mL of DMF and 3.86 g (19.48 mmol, 20-fold excess) of 4-iodobutyraldehyde is added followed by 500 μL of N,N-diisopropylethylamine (DIPEA). After five minutes the material is purified by reverse-phase HPLC on a Waters NovaPak C-18 column using a gradient elution. The gradient consisted of 90:10 eluent A to 70:30 eluent B at 75 mL per minute, over 40 minutes, where eluent A is 0.1% trifluoroacetic acid (TFA) and eluent B is 90% acetonitrile containing 0.1% TFA. The identity of the product was confirmed by electrospray mass spectrometry $M^+H^+=596$.

Example 2

Conjugation of 2-PDOX to the Anti-CD22 Antibody Humanized LL2 (hLL2)

Activation of 2-PDOX: 2-PDOX (5.95 mg; $1\times10^{-5}$ mol) is mixed with a molar equivalent of the commercially available linker 4-[N-maleimidomethyl]cyclohexane-1-carboxylhydrazide ($M_2C2H$; Pierce Chemical Co., Rockford, Ill.) (2.88 mg; $1\times10^{-5}$ mol) in 0.5 mL of dimethylsulfoxide (DMSO). The reaction mixture is heated at 50-60° C. under reduced pressure for thirty minutes. The desired product is purified by preparative RP-HPLC, using a gradient consisting of 0.3% ammonium acetate and 0.3% ammonium acetate in 90% acetonitrile, pH 4.4, to separate the desired product from most of the unreacted 2-PDOX (eluting .about.0.5 minute earlier) and from unreacted $M_2C_2H$ (eluting much earlier). The amount recovered is estimated by reference to the UV absorbance level of the sample (496 nm), versus a standard solution of 2-PDOX in acetonitrile/ammonium acetate buffer. The maleimide-activated 2-PDOX is frozen and lyophilized, if not used immediately. It is taken up in the minimum amount of DMSO when needed for future reaction with antibodies.

Reduction of hLL2 IgG: A 1-mL sample of LL2 antibody (8-12 mg/mL) at 4° C. is treated with 100 μl, of 1.8 M Tris HCl buffer, followed by three μl of 2-mercaptoethanol. The reduction reaction is allowed to proceed for 10 minutes, and the reduced antibody is purified through two consecutive spin-columns of G-50-80 Sephadex equilibrated in 0.1 M sodium acetate, pH 5.5, containing 1 mM EDTA as anti-oxidant. The product is assayed by UV absorbance at 280 nm, and by Ellman reaction with detection at 410 nm, to determine the number of thiol groups per mole of antibody. These reduction conditions result in the production of approximately 8-12' thiol groups per antibody, corresponding to complete reduction of the antibody's inter-chain disulfide bonds.

Conjugation of Activated 2-PDOX to reduced hLL2: The thiol-reduced antibody is treated with maleimido-activated 2-PDOX, without allowing the final concentration of DMSO to go above 25% in the aqueous/DMSO mixture. After reaction for 15 minutes at 4° C., the desired product is obtained free of unreacted maleimido-DOX by elution through a G-50-80 spin-column, equilibrated in 0.2 M ammonium acetate, pH 4.4, followed by percolation through a column of SM-2 Bio-Beads equilibrated in the same buffer. The product is analyzed by UV scan at 280 and 496 nm, and the molar ratio of 2-PDOX to antibody is estimated thereby. The absolute 2-PDOX-to-MAb ratio is determined by MALDI-TOF mass spectral analysis. Both UV and MS analyses indicate that a substitution ratio of 7-8 units of 2-PDOX per mole of hLL2 antibody, is obtained under this set of reaction conditions. Upon analysis by size-exclusion HPLC (GF-250 column, Bio-Rad, Hercules, Calif.) run at 1 mL/minute in 0.2 M acetate buffer, pH 5.0, with a UV detector set at 496 nm, essentially all the detected peak elutes near the retention time of the LL2 antibody. This indicates that very little free drug is present in the product. Samples of 2-PDOX-hLL2 conjugate are aliquoted into single fractions, typically of 0.1-1.0 mg, and frozen for future use, or, alternatively, they are lyophilized. They are defrosted or reconstituted, as needed, for further testing.

Example 3

Conjugation of 2-PDOX to the Anti-CD74 Antibody Humanized LL1 (hLL1)

Activation of 2-PDOX: 2-PDOX (5.95 mg; $1 \times 10^{-5}$ mol) is mixed with a molar equivalent of the commercially available linker 4-[N-maleimidomethyl]cyclohexane-1-carboxylhydrazide ($M_2C_2H$; Pierce Chemical Co., Rockford, Ill.) (2.88 mg; $1 \times 10^{-5}$ mol) in 0.5 mL of DMSO. The reaction mixture is heated at 50-60° C. under reduced pressure for thirty minutes. The desired product is purified by preparative RP-HPLC, using a gradient consisting of 0.3% ammonium acetate and 0.3% ammonium acetate in 90% acetonitrile, pH 4.4, to separate the desired product from most of the unreacted 2-PDOX (eluting .about.0.5 minute earlier) and from unreacted $M_2C_2H$ (eluting much earlier). The amount recovered is estimated by reference to the UV absorbance level of the sample (496 nm), versus a standard solution of 2-PDOX in acetonitrile/ammonium acetate buffer. The maleimide-activated 2-PDOX is frozen and lyophilized, if not used immediately. It is taken up in the minimum amount of dimethylformamide (DMF) or DMSO when needed for future reaction with antibodies.

Reduction of hLL1 IgG: A 1-mL sample of hLL1 antibody (8-12 mg/mL) at 4° C. is treated with 100 μL of 1.8 M Tris HCl buffer, followed by three μL of 2-mercaptoethanol. The reduction reaction is allowed to proceed for 10 minutes, and the reduced antibody is purified through two consecutive spin-columns of G-50-80 Sephadex equilibrated in 0.1 M sodium acetate, pH 5.5, containing 1 mM EDTA as anti-oxidant. The product is assayed by UV absorbance at 280 nm, and by Ellman reaction with detection at 410 nm, to determine the number of thiol groups per mole of antibody. These reduction conditions result in the production of approximately eight-to-ten thiol groups per antibody, corresponding to complete reduction of the antibody's inter-chain disulfide bonds.

Conjugation of Activated 2-PDOX to reduced hLL1: The thiol-reduced antibody is treated with maleimido-activated 2-PDOX with the final concentration of DMSO of 15% in the aqueous/DMSO mixture. After reaction for 15 minutes at 4° C., the desired product is obtained free of unreacted maleimido-DOX by elution through a G-50-80 spin-column, equilibrated in 0.2 M ammonium acetate, pH 4.4, followed by percolation through a column of SM-2 Bio-Beads equilibrated in the same buffer. The product is analyzed by UV scan at 280 and 496 nm, and the molar ratio of 2-PDOX to antibody is estimated thereby. The absolute 2-PDOX-to-MAb ratio is determined by MALDI-TOF mass spectral analysis. Both UV and MS analyses indicate that a substitution ratio of 7-8 units of 2-PDOX per mole of hLL1 antibody, is obtained under this set of reaction conditions. Upon analysis by size-exclusion HPLC (GF-250 column, Bio-Rad, Hercules, Calif.) run at 1 mL/minute in 0.2 M-acetate-buffer, pH 5.0, with a UV detector set at 496 nm, essentially one detected peak elutes near the retention time of the hLL1 antibody. This indicates that very little free or no drug is present in the product. Samples of 2-PDOX-hLL1 conjugate are aliquoted into single fractions, typically of 0.1-1.0 mg, and frozen for future use, or alternatively they are lyophilized. They are defrosted or reconstituted, as needed, for further testing.

Example 4

Conjugation of DOX to the Anti-CD74 Antibody hLL1

Activation of DOX: DOX ($1 \times 10^{-5}$ mol) is mixed with a molar equivalent of the commercially available linker 4-[N-maleimidomethyl]cyclohexane-1-carboxylhydrazide ($M_2C_2H$; Pierce Chemical Co., Rockford, Ill.) (2.88 mg; $1 \times 10^{-5}$ mole) in 0.5 mL of DMSO. The reaction mixture is heated at 50-60° C. for thirty minutes. The desired intermediate, shown below, is purified by preparative RP-HPLC, using a gradient consisting of 0.3% ammonium acetate and 0.3% ammonium acetate in 90% acetonitrile, pH 4.4, to separate the desired product from the unreacted DOX (eluting .about.0.5 minute earlier) and from unreacted $M_2C_2H$ (eluting much earlier).

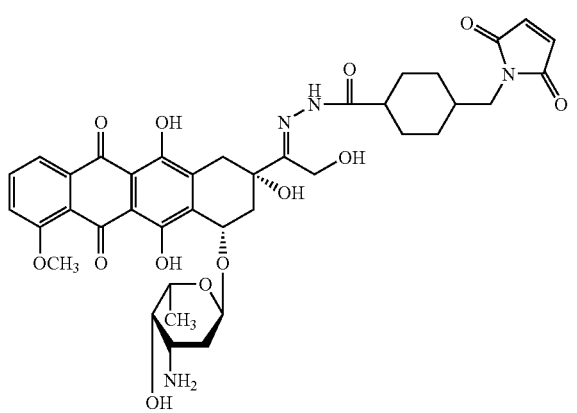

The amount of unreacted DOX is estimated by reference to the UV absorbance level of the sample (496 nm), versus a standard solution of DOX in acetonitrile/ammonium acetate buffer. The maleimide-activated DOX is frozen and lyophilized, if not used immediately. It is taken up in the minimum amount of DMF or DMSO when needed for future reaction with antibodies.

Reduction of hLL1 IgG: A 1-mL sample of hLL1 antibody (10 mg/mL) at 4° C. is treated with 100 µL of 1.8 M Tris HCl buffer, followed by three µL of 2-mercaptoethanol. The reduction reaction is allowed to proceed for 10 minutes, and the reduced antibody is purified through two consecutive spin-columns of G-50-80 Sephadex equilibrated in 0.1 M sodium acetate, pH 5.5, containing 1 mM EDTA as antioxidant. The product is assayed by UV absorbance at 280 nm, and by Ellman reaction with detection at 410 nm, to determine the number of thiol groups per mole of antibody. These reduction conditions result in the production of approximately eight-to-ten thiol groups per antibody, corresponding to complete reduction of the antibody's inter-chain disulfide bonds.

Conjugation of activated DOX to reduced hLL1: The thiol-reduced antibody is treated with maleimido-activated DOX, with a final concentration of DMSO of 15% in the aqueous/DMSO mixture. After reaction for 15 minutes at 4° C., the desired product is obtained free of unreacted maleimido-DOX by elution through a G-50-80 spin-column, equilibrated in 0.2 M ammonium acetate, pH 4.4, followed by percolation through a column of SM-2 Bio-Beads equilibrated in the same buffer. The product is analyzed by UV scan at 280 and 496 nm, and the molar ratio of DOX to antibody is estimated thereby. The absolute DOX-to-MAb ratio is determined by MALDI-TOF mass spectral analysis. The analyses indicate that a substitution ratio of 7-8 units of DOX per mole of hLL1 antibody, is obtained under this set of reaction conditions. Upon analysis by size-exclusion HPLC (GF-250 column, Bio-Rad, Hercules, Calif.) run at 1 mL/minute in 0.2 M acetate buffer, pH 5.0, with a UV detector set at 496 nm, essentially one detected peak elutes near the retention time of the hLL1 antibody. The trace (see FIG. 1; UV detector at 496 nm, set to detect DOX) shows doxorubicin-LL1 conjugate as essentially a single peak at retention time of around nine minutes, without aggregated proteinaceous species or free DOX (retention time around 14 minutes). This indicates that very little free or no drug is present in the product. Samples of DOX-hLL1 conjugate are aliquoted into single fractions, typically of 0.1-1.0 mg, and frozen for future use, or alternatively they are lyophilized. They are defrosted or reconstituted, as needed, for further testing.

Example 5

Coupling of Doxorubicin to hLL1 and Formulation of the Dox-hLL1 Conjugate

Reaction of Doxorubicin with SMCC Hydrazide. Mix 90 mg of doxorubicin ($1.56 \times 10^{-4}$ mol) and 60.23 mg of SMCC hydrazide in 13 mL of 1:2 methanol:ethanol (anhydrous), and add 10.4 µL of trifluoroacetic acid. The mixture is allowed to stir for 4 h, in the dark, at room temperature. The reaction solution is then filtered through a 0.22 micron syringe filter into a 100 mL round-bottomed flask. Seventy-five µL of diisopropylethylamine is added and the solvent evaporated on a rotary evaporator at 300° C. The residue is triturated with 4×40 mL acetonitrile followed by 1×40 mL diethyl ether and dried to a powder on the rotary evaporator under high vacuum. The powder was redissolved in 5 mL anhydrous methanol, re-evaporated to dryness as above, and then stored at −200° C. until needed.

Reduction of hLL1-IgG with Dithiothreitol. In a 20 mL round bottomed flask are mixed 8.4 mL of hLL1-IgG (10.3 mg/mL, $5.78 \times 10^{-7}$ mol), 160 µL of 0.1 M sodium phosphate buffer pH 7.5, 500 µL of 0.2 M EDTA, pH 7.0, and 290 µL of deionized water. The mixture is deoxygenated by cycling solution six times between vacuum and an argon atmosphere. A freshly prepared solution of 40 mM dithiothreitol (DTT) in water (0.015 g in 2.4 mL water, $2.3 \times 10^{-5}$ mol; 40-fold molar excess to IgG) is deoxygenated by bubbling argon through it for 10 minutes, and 640 µL of this aqueous DTT solution is added to the deoxygenated hLL1 antibody solution. The resulting mixture is incubated at 37° C. for 1 hour. The reduced antibody is purified by diafiltration (one 30K filter, under argon, at 4° C.), against deoxygenated 10 mM PBS/100 mM L-histidine, pH 7.4, buffer. The buffer is added continuously until total filtrate volume is 300 mL. The volume of the reduced hLL1 solution (hLL1-SH) is reduced to 10 mL.

Conjugation of Doxorubicin-SMCC to hLL1-SH and Purification of Conjugate. The activated doxorubicin (1.9 mL, $2.09 \times 10^{-5}$ mol, 36-fold excess to IgG) is taken up in dimethylsulfoxide (DMSO) solution and then slowly added to the hLL1-SH antibody solution (40 mL) under argon at room temperature. The final concentration of DMSO is 5%. The reaction is allowed to proceed with gentle stirring for 40 minutes at 40° C. The reaction mixture is loaded onto a BioBead™ (Bio-Rad, Richmond, Calif.) column (1.5 cm diameter×34 cm high, equilibrated with 10 mM PBS/100 mM L-histidine, pH 7.4, buffer), and run through at 2 mL/min. The product conjugate is concentrated in an Amicon filtration unit and filtered through a 0.22 micron syringe filter prior to formulation for lyophilization.

Conjugate Formulation and Lyophilization. To 40 mL of the above hLL1-dox solution are added 8 mL of 0.5M mannitol solution in water, and 0.48 mL of 1% polysorbate 20, resulting in final concentrations of 1.64 mg/mL hLL1-dox, 82.5 mM mannitol, and 0.01% polysorbate-20. Samples are lyophilized in 1 mg and 10 mg dox-hLL1 quantities (3 and 10 mL vials, respectively), frozen on dry ice, and lyophilized under vacuum over 48 h. Vials are stoppered under vacuum, and stored sealed at −20° C., in the dark, for future use.

Example 6

Preparation of Morpholino-DOX and Cyanomorpholino-DOX Conjugates of Antibodies

Morpholino-DOX and cyanomorpholino-DOX are prepared by reductive alkylation of doxorubicin with 2,2'-oxybis[acetaldehyde], using the procedure of Acton, et al. (J. Med. Chem. 27:638-645 (1984)).

These DOX analogs were coupled with $M_2C_2H$ in the same manner as described above for the DOX and 2-PDOX analogs. Cyanomorpholino-DOX was coupled with 10% molar excess of the hydrazide in anhydrous methanol (instead of DMSO) overnight at the room temperature. Solvent removal, followed by flash chromatography furnished the hydrazone. Electrospray mass spectral analysis: M+H m/e 872, M+Na 894; M–H 870. In a similar fashion, morpholino-DOX was derivatized to its hydrazone using SMCC-hydrazide using 1.5 equivalent of the reagent in anhydrous methanol for 4 h, and the product was purified by flash chromatography. Electrospray mass spectrum: M+H m/e 847, M–H m/e 845, M+Cl m/e 881.

Interchain disulfide bonds of antibodies were reduced to free thiols as described above in Examples 2-4, to generate disulfide-reduced antibodies, and conjugates were prepared using the same methods as described in Examples 2, 3, and 4. The following antibody conjugates of morpholino-DOX and cyanomorpholino-DOX were prepared:

Morpholino-DOX-Antibody Conjugates:
mRS7 conjugate: drug-to-antibody substitution ratio: 6.4:1.
mMN-14 conjugate: drug-to-antibody substitution ratio: 8.9:1.
Cyanomorpholino-DOX-Antibody Conjugates:
mRS7 conjugate: drug-to-antibody substitution ratio: 5.3:1.
mMN-14 conjugate: drug-to-antibody substitution ratio: 7.0:1.

Example 7

In Vitro Efficacy of Anthracycline-Antibody Conjugates

Figure 2:
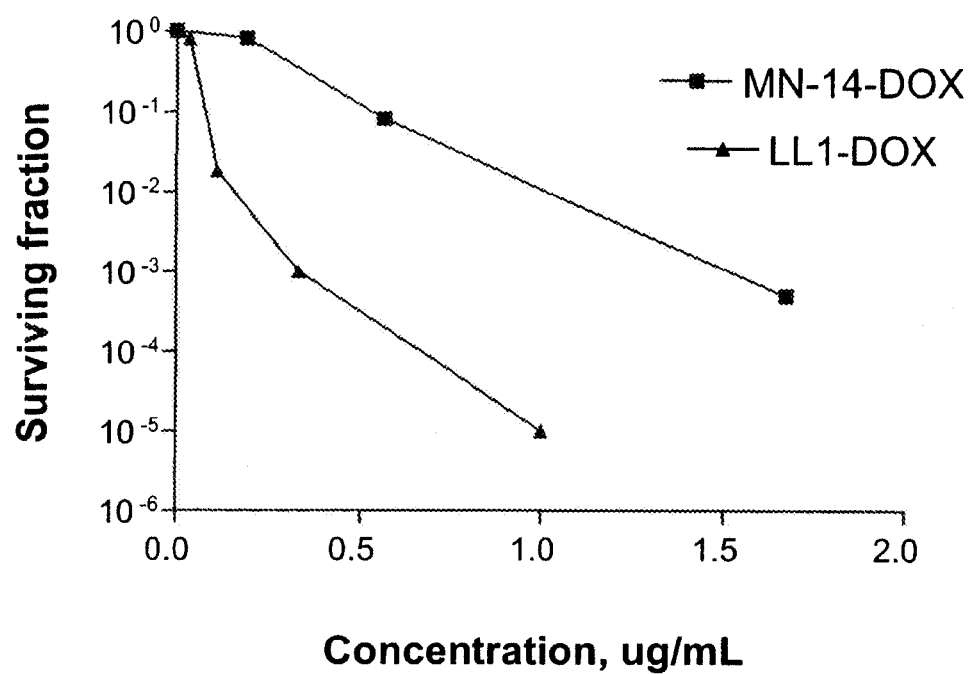
FIG. 2 illustrates the in vitro efficacy of the DOX-LL1 conjugate against Burkitt lymphoma Raji cells, versus a DOX conjugate of the non-targeting MN-14 antibody at a concentration of drug-antibody conjugate of 1 μL/mL. The DOX-LL1 conjugate shows a three-order of magnitude difference in the fraction of surviving cells, in comparison to the DOX-MN-14 conjugate.

Raji B-lymphoma cells were obtained from the American Type Culture Collection (ATCC, Rockville, Md.), and were grown in RPMI 1640 medium containing 12.5% fetal bovine serum (Hyclone, Logan, Utah), supplemented with glutamine, pyruvate, penicillin and streptomycin (Life Technologies, Grand Island, N.Y.). Briefly, $3.75 \times 10^5$ cells were incubated for 2 days with the indicated concentration of drug-antibody conjugate in 1.5 mL of tissue culture medium in wells of 24-well plates. The cells were then transferred to T25 flasks containing 20 ml of medium, and incubated for up to 21 days, or until the cells had multiplied 16-fold. Viable cell counts using Trypan blue were performed at day 0, day 2, and then every 3-5 days. From the growth rate of untreated cells, the doubling time was calculated, and the Fraction Surviving was calculated from the time required for treated cells to multiply 16-fold, assuming that the doubling time was not affected by treatment. A single remaining viable cell could be readily detected. At a concentration of drug-antibody conjugate of 1 μg/mL the DOX-LL1 conjugate showed a three-orders of magnitude difference in the fraction of surviving cells, in comparison to the DOX-MN-14 conjugate. See FIG. 2.

Example 8

Treatment of Tumor-Bearing Animals with Anthracycline-Antibody Conjugates

Figure 3:
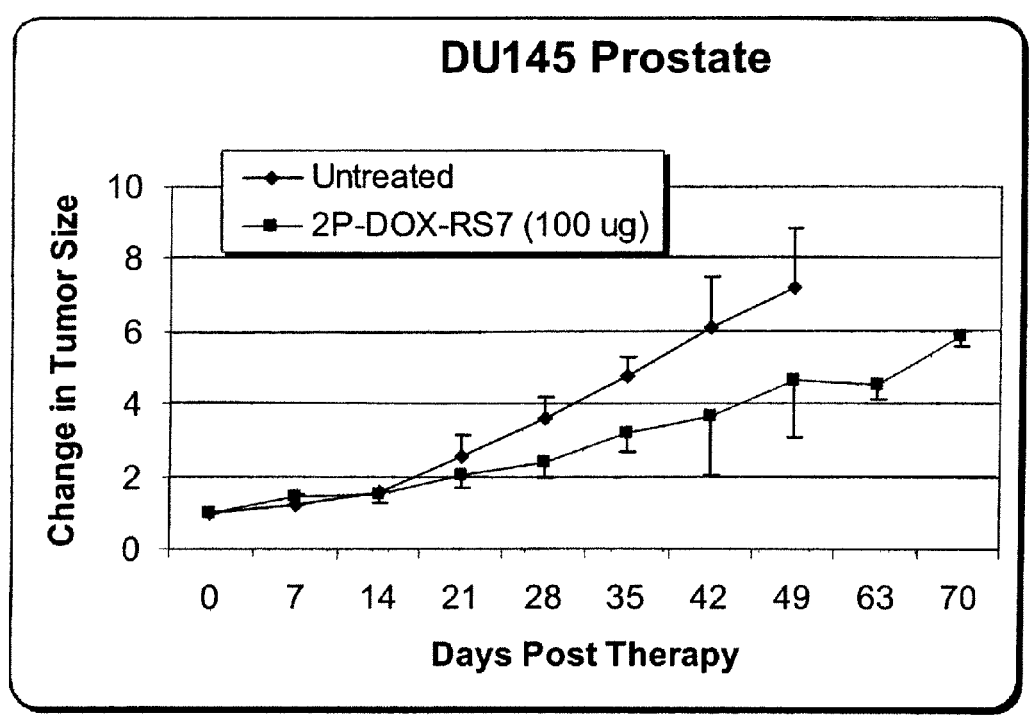
FIG. 3 is illustrates the efficacy of a single 100 μg dose of 2-PDOX-RS7 conjugate in the DU145 prostate xenograft model in nude mice.

Treatment in a solid tumor xenograft model. Groups of athymic nude mice were injected subcutaneously with DU145 human prostate cancer cells. After approximately two weeks, when palpable prostate tumor xenografts had grown in the animals, half were treated with a single dose of the drug-antibody conjugate 2-PDOX-RS7, and half were left untreated (controls). FIG. 3, shows the growth of the tumor xenografts in untreated mice versus the growth of xenografts in mice treated with 2-PDOX-RS7. It shows a therapeutic effect for animals treated with the drug-antibody conjugate, in terms of delayed growth of the xenografts.

Figure 4:
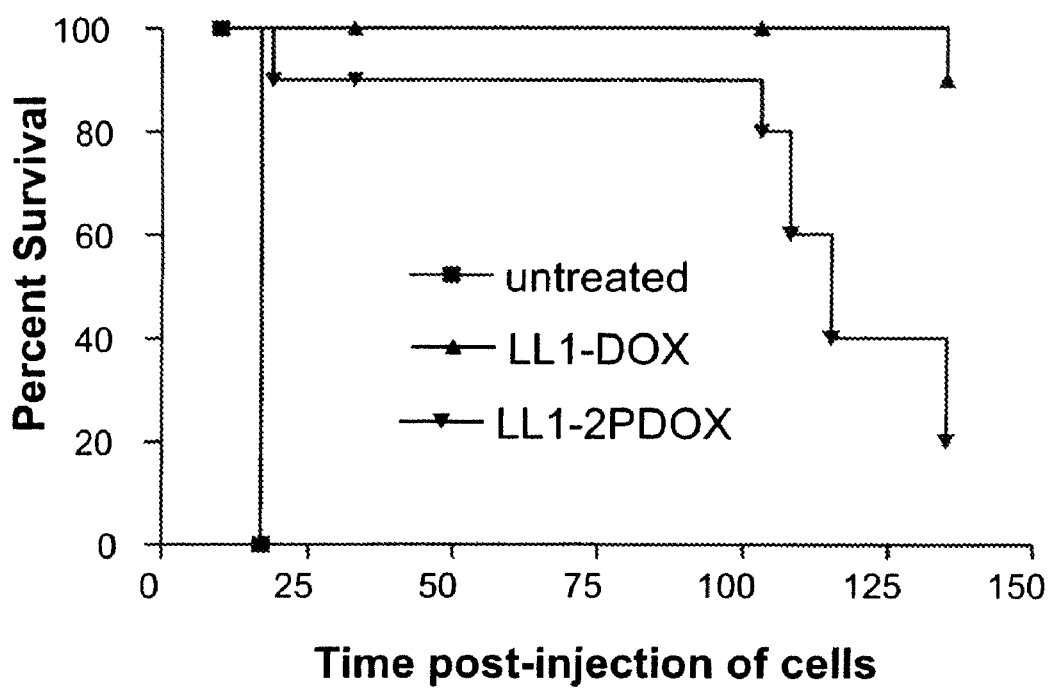
FIG. 4 illustrates the efficacy of single doses of 2-PDOX- and DOX-conjugates of the LL1 antibody in the aggressive RAJI/SCID mouse systemic tumor model. Animals were injected i.v. with Raji B-cell lymphoma cells, and treated five days later with the conjugates designated in the figure.

Treatment of systemic cancer in an animal model. NCr-SCID mice, in groups of ten animals, were each given an intravenous injection of a suspension of $2.5 \times 10^6$ cells of the human Burkitt's B-cell lymphoma cell line, Raji, by tail-vein injection. Five days later, animals were left untreated or treated with single doses of either 350 μg DOX-LL1 or 150 μg 2-PDOX-LL1. FIG. 4 shows the result of the experiment. Untreated animals become paralyzed and die at around 23 days post-injection of the Raji cells, from systemic cancer. Animals treated with DOX- and 2-PDOX-conjugates of the LL1 antibody survived over an extended period corresponding to around a four-fold increase in life expectancy for the 2-PDOX-LL1-treated animals, and an even greater increased life expectancy for the DOX-LL1-treated animals.

Figure 5:
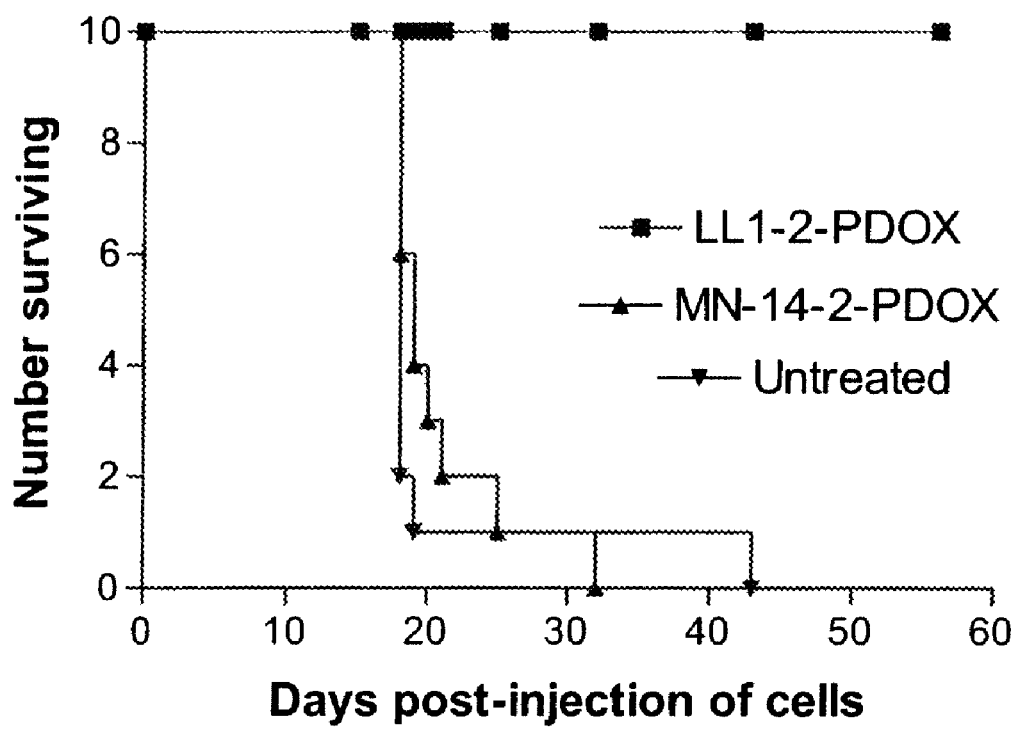
FIG. 5 illustrates the efficacy of a single dose of 2-PDOX-LL1 antibody in the aggressive RAJI/SCID mouse systemic tumor model, compared to untreated controls given no conjugate, or a group of animals given the non-targeting control conjugate, 2-PDOX-MN-14.

Treatment of systemic cancer in an animal model. NCr-SCID mice, in groups of ten animals, were each given an intravenous injection of a suspension of $2.5 \times 10^6$ cells of the human Burkitt's B-cell lymphoma cell line, Raji, by tail-vein injection. Five days later, animals were left untreated or treated with single doses of either 150 μg 2-PDOX-LL1 or 150 μg of 2-PDOX-MN-14 (non-specific control antibody conjugate). FIG. 5 shows the result of the experiment. Untreated animals become paralyzed and die at around 23 days post-injection of the Raji cells, from systemic cancer, as do animals treated with the 2-PDOX-MN-14 conjugate. Animals treated with the 2-PDOX-LL1 antibody conjugate survived over an extended period.

Example 9

Molecular Cloning and Sequence Elucidation for LL1 Heavy and Light Chain Variable Regions The Vk gene of mLL1 was obtained by RT-PCR using VK5'-4 and VK1 FOR primers as described by Leung et al. 1993 and Orlandi et al. (PNAS 86:3833-3837. (1989), respectively, and cloned into pCR2.1 AT-cloning vector (Invitrogen). Multiple clones were sequenced to eliminate possible errors resulted from PCR reaction. The majority of clones contained an identical murine V sequence, which was designated as LL1Vk (not shown). Comparison with other mouse Vk sequences revealed LL1Vk is a member of the kappa light chain subclass II.

Since RT-PCR failed to yield a full-length sequence encoding a mouse VH gene, a second cloning approach, rapid amplification of cDNA 5'-ends (5'-RACE) was employed. The adaptor-ligated cDNA prepared from LL1 hybridoma cells was amplified by PCR using a universal anchor primer (Life Technologies) and a gene specific primer, CH-1B (Leung et al. 1994), which anneals to the CH1 region of the murine heavy chain. The major PCR species of 650 by resulting from PCR was cloned into pCR2.1 AT-cloning vector and multiple clones were sequenced by DNA sequencing. The PCR product contained a full-length VH sequence (not shown) flanked by the sequences of non-coding and secretion signal peptide at the '5-end and partial coding sequence for the CH1 domain of 1 chain. No defective mutation was found within the sequence encoding the VH, which was designated as LL1VH. Comparison of LL1VH with other mouse VH sequences revealed that it belonged to mouse heavy chain subgroup miscellaneous (Kabat et al., 1991). By comparing the amino acid sequences of LL1VH and Vk with murine Ab V genes in Kabat database and following Kabat's definition, the CDR regions of mLL1VH and Vk were identified (see FIGS. 6A and 6B, boxed sequences).

Example 10

Construction of the Expression Vector for Chimeric LL1

To evaluate the authenticity of the cloned Fv for LL1, a chimeric LL1 (cLL1) was constructed and expressed. The nucleotide residues 7-12 of LL1Vk were modified to a PvuII restriction site, CAGCTG, by PCR with primers LL1 VK-PvuII and VK1 FOR. The resulting PCR product was digested with PvuII and BglII (partially, due to the presence of an internal BglII site in the Vk) and force-cloned into a pBR327-based staging vector (digested with PvuII and BclI), VKpBR2, which contained the same Ig promoter, signal peptide sequence and convenient restriction sites to facilitate in-frame ligation of the VK PCR product as used by Orlandi et al., 1989 and Leung et al., 1994.

```
LL1VK-PvuII                              (SEQ ID NO: 17)
5'GAT GTT CAG CTG ACC CAA ACT CCA CTC TCC-3'
```

Similarly, the nucleotide sequences at positions 10-15 and 345-351 of LL1VH were converted to PstI and BstEII, respectively, by PCR with primers LL1 B-1 and LL1F-1. The VH PCR product was then digested with PstI and BstEII and ligated into PstI and BstEII digested VHpBS2, a pBluescript-based staging vector containing a signal peptide sequence and convenient restriction sites to facilitate in-frame ligation of the VH PCR product {Orlandi, Gussow, et al., 1989 741/id}, modified from VHpBS (Leung, S. O., Shevitz, J., Pellegrini, M. C., Dion, A. S., Shih, L. B., Goldenberg, D. M., and Hansen, H. J. (1994)).

```
LL1B-1                                   (SEQ ID NO: 18)
5'-CAG ATC CAG CTG CAG CAG TCT GGA CCT GAG-3'

LL1F-1                                   (SEQ ID NO: 19)
5'-GA GAC GGT GAC CAG AGT CCC TTG GCC CCA A-3'
```

The sequences of both cLL1VH and Vk were confirmed by DNA sequencing and shown in FIGS. 6A and 6B, respectively.

The fragment containing the Vk sequences of cLL1, together with the signal peptide sequences, were excised from LL1 VKpBR2 by double restriction digestion with XbaI and BamHI. The ~550 by Vk fragments was then subcloned into the XbaI/BamHI site of a mammalian expression vector, pdHL2. The resulting vector was designated as cLL1VkpdHL2. Similarly, the ca. 750 by fragments containing the LL1VH, together with the signal peptide sequences, were excised from LL1VHpBS2 by XhoI and BamHI digestion and isolated by electrophoresis in an agarose gel. The fragment was subcloned into the XhoI and HindIII site of cLL1VkpdHL2 with the aid of linker compatible with both BamHI and HindIII ends, resulting in the final expression vector, designated as cLL1pdHL2.

Example 11

Transfection and Expression of cLL1

Approximately 30 µg of cLL1pdHL2 was linearized by digestion with SalI and transfected into Sp2/0-Ag14 cells by electroporation. The transfected cells were plated into 96-well plate for 2 days and then selected for MTX resistance. Supernatants from colonies surviving selection were monitored for chimeric antibody secretion by ELISA assay. Positive cell clones were expanded and cLL1 was purified from cell culture supernatant by affinity chromatography on a Protein A column.

Example 12

Binding Activity Assays

Figure 8:
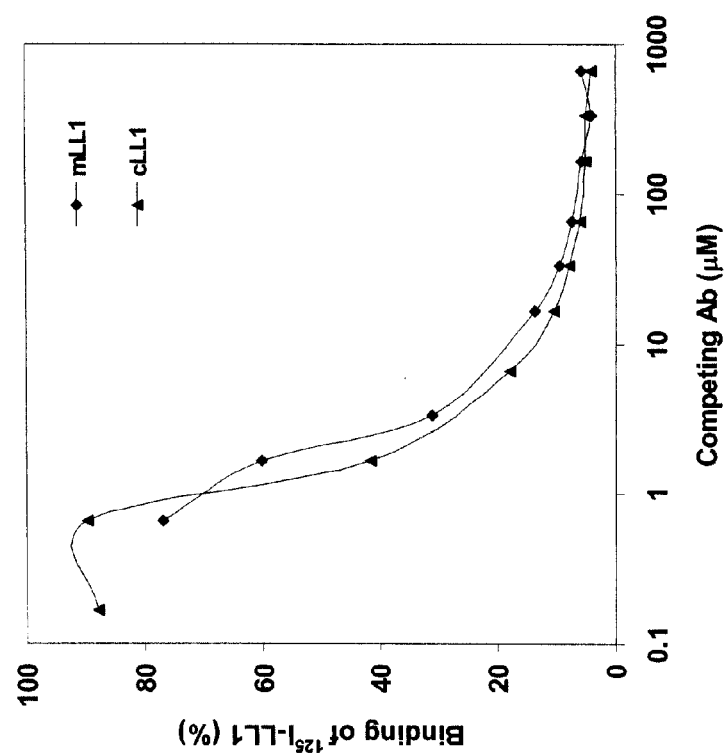
FIG. 8 shows the result of a competitive cell surface binding assay to compare the binding affinity of cLL1 with that of murine LL1. Varying concentrations of cLL1 (triangles) or mLL1 (diamonds) were mixed with a constant amount of $^{125}$I-labeled mLL1 and incubated with Raji cells at 4° C. for 1 h. The cell surface bound radiolabeled mLL1 was counted after washing. cLL1 and the murine LL1 competed equally well for the binding of radiolabeled LL1 to Raji cells, confirming the cloned V genes are authentic.

A competition cell binding assay was carried out to assess the immunoreactivity of cLL1 relative to the parent mLL1. A constant amount of $^{125}$I-labeled mLL1 (100,000 cpm) was incubated with Raji cells in the presence of varying concentrations of cLL1 or mLL1 at 4° C. for 1-2 h. The radioactivity associated with cells was determined after washing. As shown in FIG. 8, cLL1 antibody exhibited comparable binding activity as that of mLL1, confirming the authenticity of the cloned V genes.

The results were confirmed by a second competition assay based on flow cytometry. Briefly, using Raji cells as before and varying the concentration of one antibody relative to other, as before, the amount of bound mLL1 or cLL1 was determined with FITC-labeled anti-mouse Fc or anti-human Fc antibodies followed by analysis using flow cytometry.

An ELISA competitive binding assay were carried out in a Raji cell membrane coated plate to assess the immunoreactivity of cLL1 relative to the parent mLL1. Raji cell membrane fraction was prepared by sonication and centrifugation. The crude membrane extracts were coated in 96-well flat bottomed PVC plates by centrifugation and fixed with 0.1% glutaraldehyde. A constant amount of the biotinylated mLL1 mixed with varying concentrations of mLL1 or cLL1 was added to the membrane coated wells and incubated at room temperature for 1-2 h. After washing, HRP-conjugated streptavidin was added and incubated for 1 h at room temperature. The amount of HRP-conjugated streptavidin bound to the membrane-bound biotinylated mLL1 was revealed by reading at A490 nm after the addition of a substrate solution containing 4 mM ortho-phenylenediamine dihydrochloride and 0.04% $H_2O_2$.

Example 13

Choice of Human Frameworks and Sequence Design for the Humanization of LL1 Monoclonal Antibody By comparing the variable (V) region framework (FR) sequences of cLL1 to that of human antibodies in the Kabat data base, the FRs of cLL1VH and Vk were found to exhibit the highest degree of sequence homology to that of the human antibodies, RF-TS3VH and HF-21/28 Vk, respectively. The amino acid sequences are provided for comparison in FIGS. 6A and 6B. The FRs of RF-TS3 VH and the HF-21/28 Vk were selected as the human frameworks onto which the CDRs for LL1 VH and Vk were grafted, respectively. The FR4 sequence of NEWM, however, rather than that of RF-TS3, was used to replace the RF-TS3 FR4 sequence for the humanization of the LL1 heavy chain. See FIG. 6A. A few amino acid residues in the LL1 FRs that are close to the putative CDRs were maintained in hLL1 based on the guidelines described previously (Qu et al., Clin. Cancer Res. 5:3095s-3100s (1990)). These residues are L46, F87 and Q100 of VK (FIG. 6B) and I36, K37, Q46, A68, F91 and S93 of VH (FIG. 6A). FIGS. 6A and 6B compare the human, chimeric and humanized VH and Vk amino acid sequences. The dots indicate the residues in the cLL1 and hLL1 that are identical to the corresponding residues in the human VH and Vk sequences. The DNA and amino acid sequences of hLL1VH and Vk are shown in FIGS. 7A and 7B, respectively.

Example 14

PCR/Gene Synthesis of the Humanized V Genes

A modified strategy as described by Leung et al. (Leung et al, 1994) was used to construct the designed Vk and VH genes for hLL1 using a combination of long oligonucleotide synthesis and PCR. For the construction of the hLL1VH domain, two long oligonucleotides, hLL1VHA (176mer) and hLL1VHB (165-mer) were synthesized on an automated DNA synthesizer (Applied Biosystems). The hLL1VHA sequence represents nt 20 to 195 of the hLL1VH domain:

```
                                          (SEQ ID NO: 20)
5'-GGTCTGAGTT GAAGAAGCCT GGGGCCTCAG TGAAGGTTTC

CTGCAAGGCT TCTGGATACA CCTTCACTAA CTATGGAGTG

AACTGGATAA AGCAGGCCCC TGGACAAGGG CTTCAGTGGATGGGCTG

GAT AAACCCCAAC ACTGGAGAGC AACATTTGA TGATGACTTC

AAGGGA-3'
```

The hLL1VHB sequence represents the minus strand of the hLL1VH domain complementary to nt 173 to 337:

```
                                          (SEQ ID NO: 21)
5'-TCCCTTGGCC CCAATAAGCA AACCAGGCTT CGTTTTTACC

CCTCGATCTT GAACAGAAAT ACACGGCAGT GTCGTCAGCC

TTTAGGCTGC TGATCTGGAG ATATGCCGTG CTGACAGAGG

TGTCCAAGGA GAAGGCAAAT CGTCCCTTGA AGTCATCATC

AAATG-3'
```

The 3'-terminal sequences (22 nt residues) of hLL1 VHA and B are complementary to each other. Under defined PCR condition, 3'-ends of hLL1 VHA and B anneal to form a short double stranded DNA flanked by the rest of the long oligonucleotides. Each annealed end serves as a primer for the transcription of the single stranded DNA, resulting in a double strand DNA composed of the nt 20 to 337 of hLL1VH. This DNA was further amplified in the presence of two short oligonucleotides, hLL1VHBACK and hLL1VHFOR to form the full-length hLL1VH.

```
hLL1VHBACK                                (SEQ ID NO: 22)
5'-GTG GTG CTG CAG CAA TCT GGG TCT GAG TTC AAG AAG

CT-3' hLL1VHFOR                                 (SEQ ID NO: 23)
5'-AAG TGG ATC CTA TAA TCA TTC CTA GGA TTA ATG-3'
```

A minimal amount of hLL1VHA and B (determined empirically) was amplified in the presence of 10 µl of 10×PCR Buffer (500 mM KCl, 100 mM Tris-HCl buffer, pH 8.3, 15 mM MgCl$_2$), 2 mol of hLL1VHBACK and hLL1VHFOR, and 2.5 units of Taq DNA polymerase (Perkin Elmer Cetus, Norwalk, Conn.). This reaction mixture was subjected to 3 cycles of PCR reaction consisting of denaturation at 94° C. for 1 minute, annealing at 45° C. for 1 minute, and polymerization at 72° C. for 1.5 minutes, and followed by 27 cycles of PCR reaction consisting of denaturation at 94° C. for 1 minute, annealing at 55° C. for 1 minute, and polymerization at 72° C. for 1 minute. Double-stranded PCR-amplified product for hLL1VH was gel-purified, restriction-digested with PstI and BstEII and cloned into the complementary PstI/BstEII sites of the heavy chain staging vector, VHpBS2.

For constructing the full length DNA of the humanized VK sequence, hLL1VKA (159-mer) and hLL1VKB (169-mer) were synthesized as described above. hLL1VKA and B were amplified by two short oligonucleotides hLL1 VKBACK and hLL1VKFOR as described above.

The hLL1 VHA sequence represents nt 16 to 174 of the hLL1VH domain.

```
                                          (SEQ ID NO: 24)
5'-CAGTCTCCAC TCTCCCTGCC CGTCACCCTT GGACAGCCGG

CCTCCATCTC CTGCAGATCA AGTCAGAGCC TTGTACACAG

AAATGGAAAC ACCTATTTAC ATTGGTTTCA GCAGAGGCCA

GGCCAATCTC CAAGGCTCCT GATCTACACA GTTTCCAAC-3'
```

The hLL1VHB sequence represents the minus strand of the hLL1VH domain complementary to nt 153 to 321.

```
                                          (SEQ ID NO: 25)
5'-TGTCCCAGCA CCGAACGTGG GAGGAACATG TGAACTTTGA

GAGCAGAAAT AAACCCCAAC ATCCTCAGCC TCCACCCTGC

TGATTTTCAG TGTGAAATCA GTGCCTGACC CACTGCCGCT

GAATCTGTCT GGGACCCCAG AAAATCGGTT GGAAACTGTG

TAGATCAGG-3' hLL1VKBACK                                (SEQ ID NO: 26)
5'-GAT GTT CAG CTG ACT CAG TCT CCA CTC TCC CTG-3' hLL1VKFOR                                 (SEQ ID NO: 27)
5'-G TTA GAT CTC CAG TCG TGT CCC AGC ACC GAA CG-3'
```

Gel-purified PCR products for hLL1Vk were restriction-digested with PvuII and BglIII and cloned into the complementary PvuI/BclI sites of the light chain staging vector, VKpBR2. The final expression vector hLL1pdHL2 was constructed by sequentially subcloning the Xba1-BamHI and XhoI/BamHI fragments of hLL1Vk and VH, respectively, into pdHL2 as described above.

Example 15

Transfection, Expression and Binding Activity Assays for hLL1

The methods for expression and binding activity assays for hLL1 were same as described for cLL1.

Figure 9:
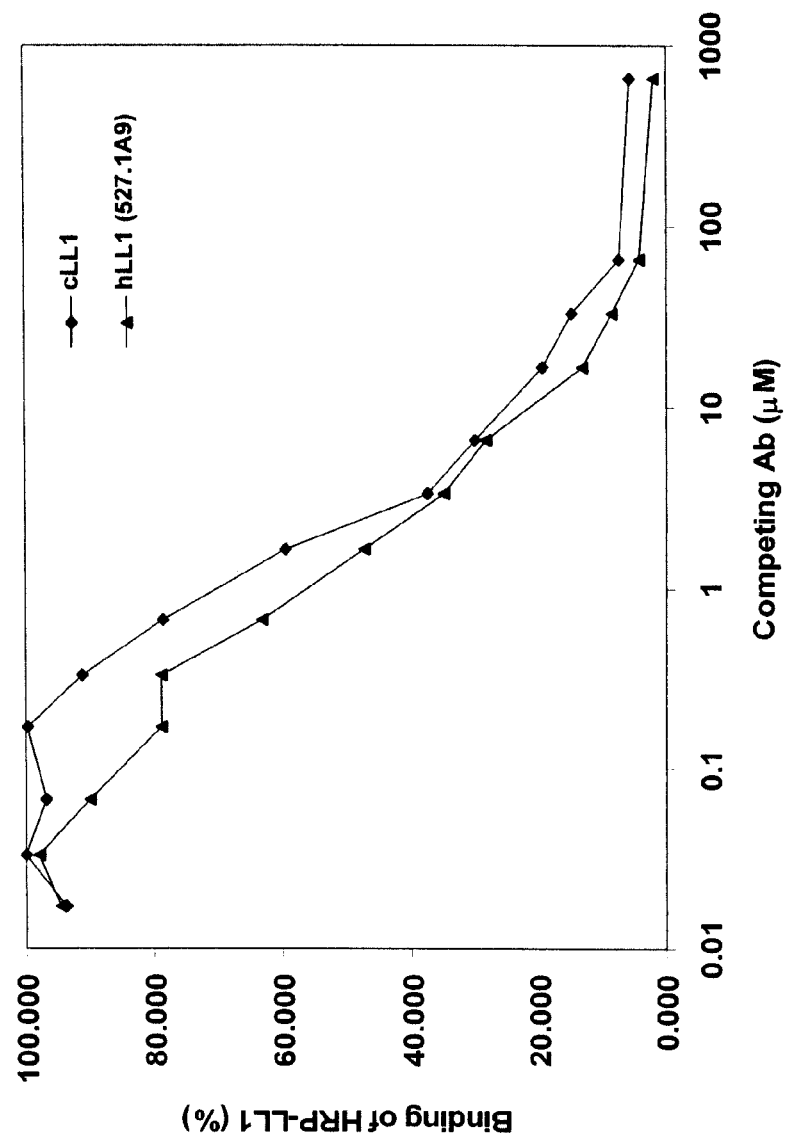
FIG. 9 shows the result of a competitive binding assay in Raji cell membrane coated micro wells to compare the binding affinity of hLL1 with that of cLL1. Varying concentrations of hLL1 (triangles) or cLL1 (diamonds) were mixed with a constant amount of HRP conjugated LL1 and incubated in 96-well microtitration plate coated with Raji membrane extracts at room temperature for 1 h. The membrane bound HRP-LL1 was measured. hLL1 and cLL1 competed equally well for the binding of HRP-LL1, indicating the binding specificity and affinity of antibody LL1 are preserved in the humanized LL1.

An ELISA competitive binding assay using Raji cell membrane extract coated plates was developed to assess the immunoreactivity of hLL1. The Raji cell membrane fraction was prepared by sonication and centrifugation. The crude membrane extracts were coated in 96-well flat bottomed PVC plates by centrifugation and fixed with 0.1% glutaraldehyde. A constant amount of the biotinylated mLL1 mixed with varying concentrations of mLL1 or cLL1 was added to the membrane coated wells and incubated at room temperature for 1-2 h. After washing, HRP-conjugated streptavidin was added and incubated for 1 h at room temperature. The amount of HRP-conjugated streptavidin bound to the membrane bound biotinylated mLL1 was revealed by reading $A_{490\,nm}$ after the addition of a substrate solution containing 4 mM ortho-phenylenediamine dihydrochloride and 0.04% $H_2O_2$. As shown by the competition assays in FIG. 8, mLL1 and cLL1 antibodies exhibited similar binding activities. Likewise, the competition assays in FIG. 9 show that hLL1 and cLL1 antibodies exhibited similar binding activities.

Example 16

Internalization of hLL1

Figure 10:
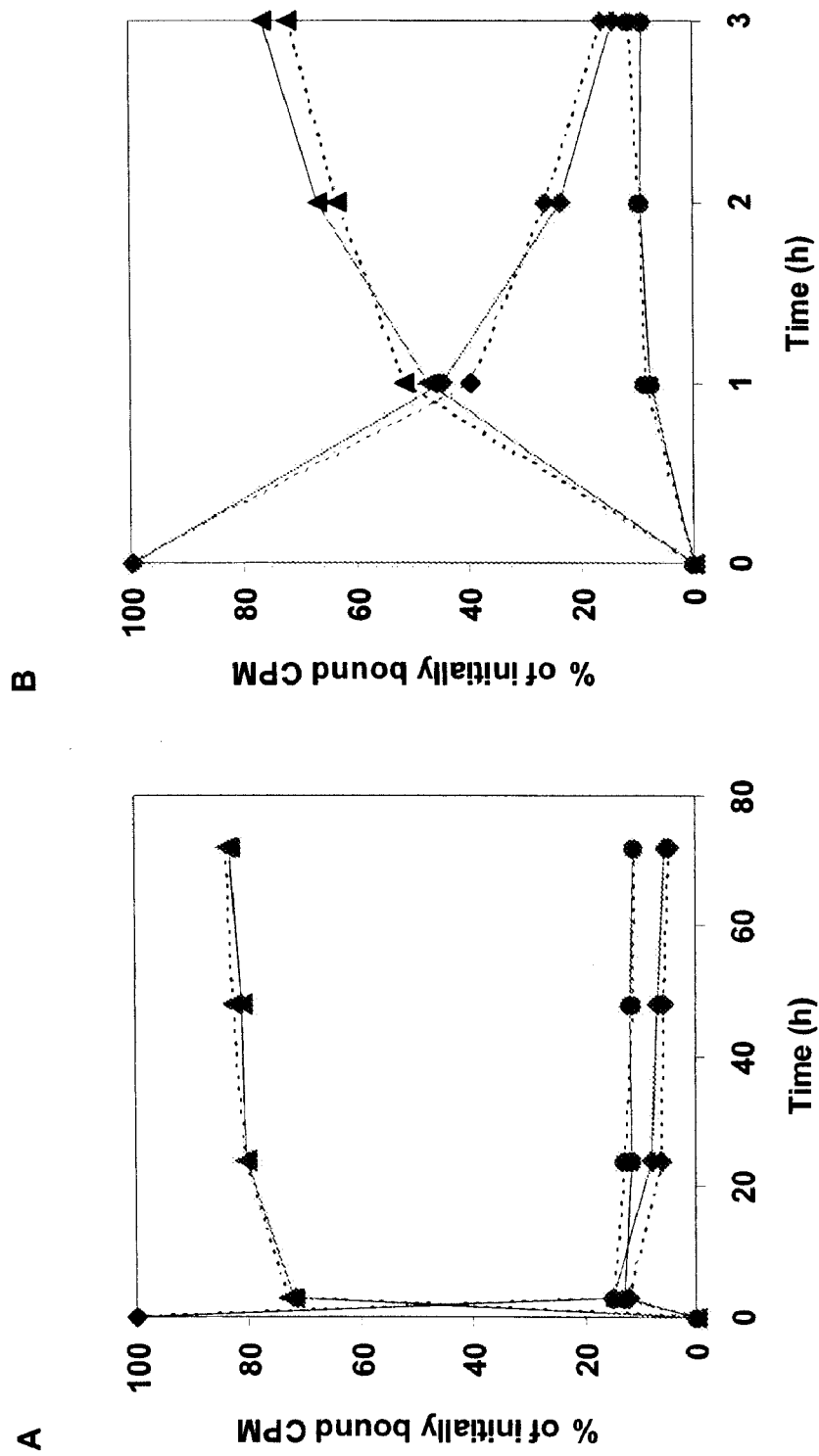
FIG. 10 shows the fate of $^{125}$I-labeled hLL1 and mLL1 bound to the surface of Raji cells. The radiolabeled hLL1 (solid line with symbols) or mLL1 (dotted line with symbols) was incubated with Raji cells and unbound antibodies were removed by washing. The cells were then cultured as normal and the radiolabeled antibodies associated with cells (diamond lines), secreted into medium (triangle lines) or degraded (circle lines) were measured at indicated time point.

A standard antibody processing assay was used to evaluate the internalization and metabolism of hLL1 in Raji cells (Hansen et al., 1996). Cells ($10^7$) were incubated in 1 ml of tissue culture medium containing $^{125}$I-labeled hLL1 or LL1 ($10^7$ cpm) for 1 h at 37° C. To ensure the specificity of Ab binding, controls of 1/10 sample size (cells, radioactivity and medium) were set up in every experiment with and without excess unlabeled Ab (final concentration of 100 μg/ml). After the binding incubation, unbound radioactivity was removed by washing. The specificity controls were counted. In all experiments, the binding of radioactivity to cells was at least 90% blocked by the unlabeled Ab. The cells were then resuspended in 30 ml of fresh medium and dispensed in a 24-well plate with 1.5 ml/well. Samples of 1.5 ml were saved for radioactivity determination, which was the initially bound cpm. The plate was incubated in a $CO_2$ incubator. At 3, 24, 48, and 72 h, the cells were collected as follows. Cells were resuspended by repeated pipetting and transferred to conical tubes. The wells and pipette were rinsed with 1 ml fresh culture medium, which was added to the initial cell suspension collected. The tube was centrifuged for 10 min at 600× g and 1 ml of supernatant was carefully collected (40% of the total supernatant) and counted for radioactivity. BSA was added as carrier protein to a final concentration of 1% and the protein was precipitated with 5 ml of cold 10% (w/v) trichloroacetic acid (TCA). After incubation for 30 min at 4° C. and centrifugation for 15 min at 5000×g, the supernatant was discarded and the precipitated protein was counted for radioactivity. The radiolabeled protein that was not precipitated by TCA was considered degraded, and precipitated radioactive protein was considered intact. The cell pellet was counted for the radioactivity remaining in the cells after being washed. Radioactivity in each fraction was expressed as a percentage of that initially bound. As shown in FIG. 10A, hLL1 showed similar rapid internalizing and catabolic properties as murine LL1 after binding to the surface of Raji cells, i.e. almost all of the bound radioactivity was catabolized and released into the supernatant within 3 h. This is much faster than with other internalizing Abs, such as anti-CD22 and anti-CD19 (Hansen et al., 1996). The studies with early time points confirmed the similar processing patterns of hLL1 and mLL1. Most catabolism was accomplished within one hour (FIG. 10B).

Example 17

Cytotoxicity of hLL1

Figure 11:
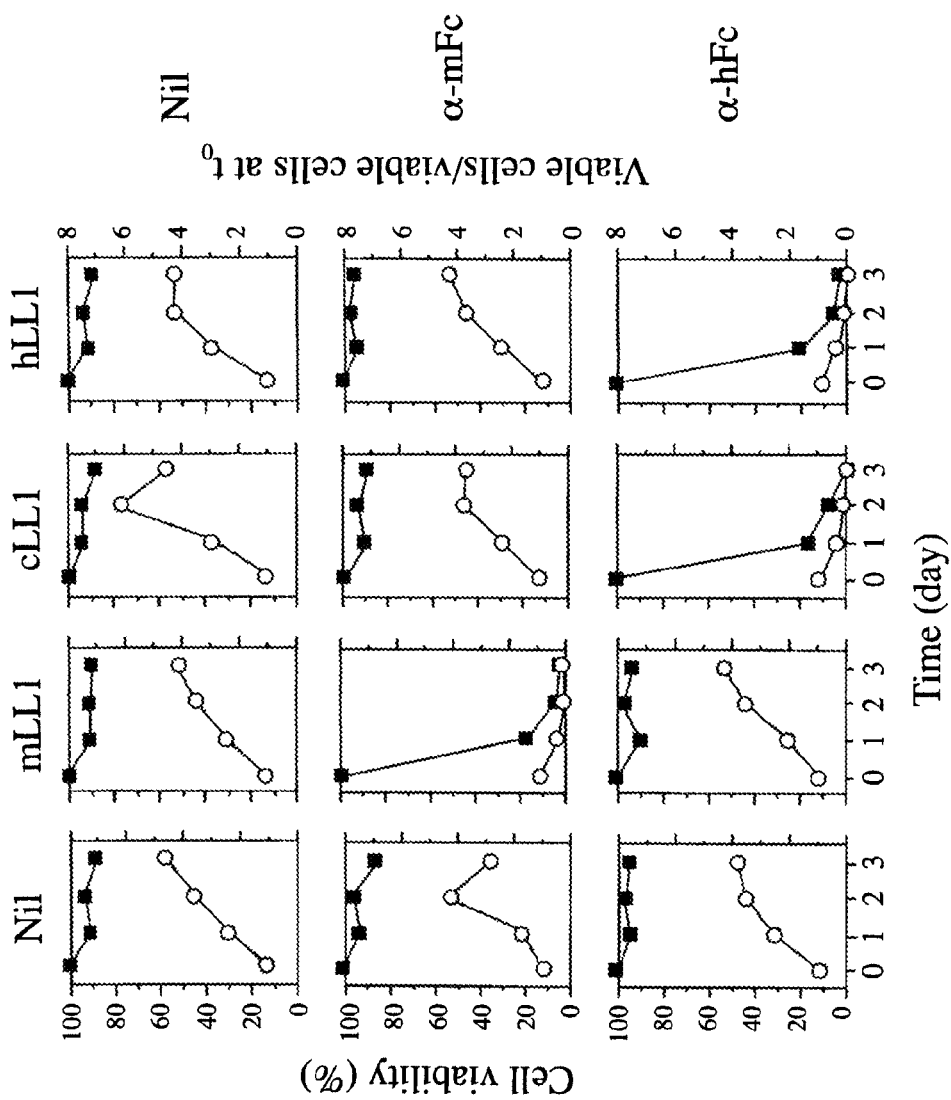
FIG. 11 shows the cytotoxicity effect of crosslinked LL1 antibodies on Raji cells. 5×10$^5$ Raji cells were seeded at day 0 in 1 ml of culture medium containing (as indicated on top of the panels) 5 μg/ml of mLL1, cLL1 or hLL1, or no antibody (Ni1), with 50 μg/ml of -mFc or -hFc Ab, or without any crosslinker (Ni1), indicated at right side of panels. The numbers of total and viable cells were counted daily for 3 days. Percentage of viable cells (squares) and the ratio of viable cells over the viable cells at time zero (diamonds) were calculated and plotted against culture time.
Figure 12:
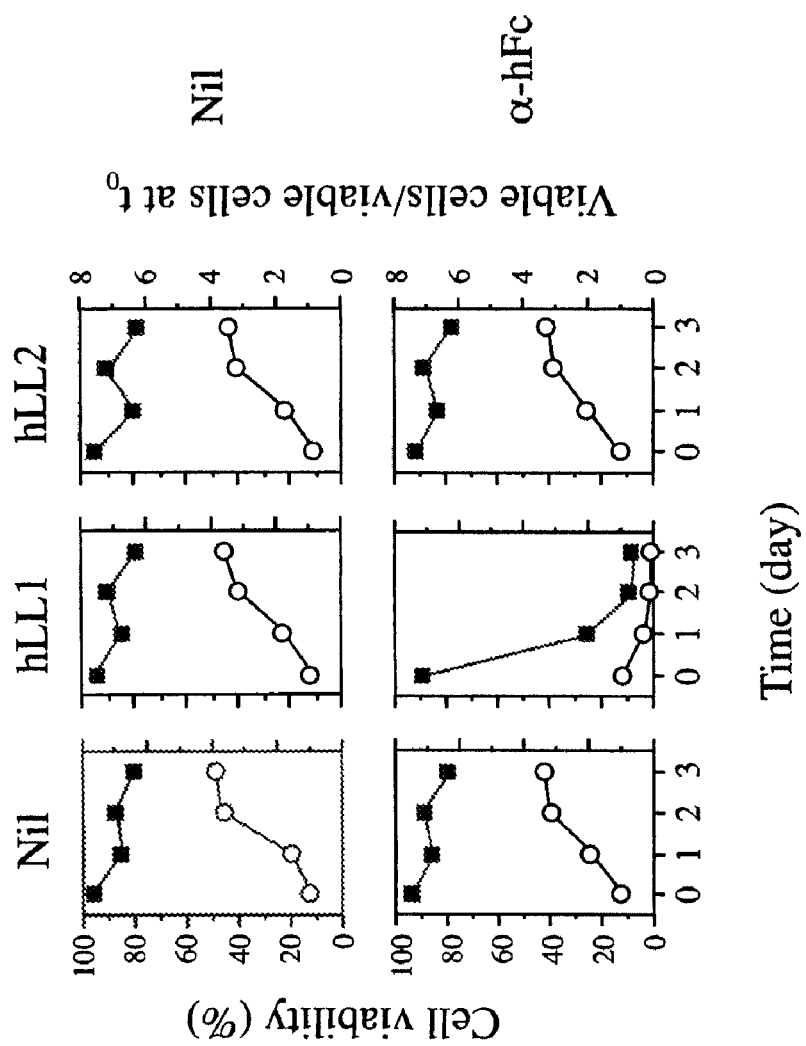
FIG. 12 shows the cytotoxicity effect of crosslinked hLL1 on Daudi cells. 5×10$^5$ Daudi cells were seeded at day 0 in 1 ml of culture medium containing (as indicated on top of the panels) 5 μg/ml of hLL1, or hLL2 (an anti-CD22, internalizing Ab), or no any Ab (Ni1), with 50 μg/ml of -hFc Ab, or without (Ni1), indicated at right side of panels. The numbers of total and viable cells were counted daily for 3 days. Percentage of viable cells (squares) and the ratio of viable cells over the viable cells at time zero (diamonds) were calculated and plotted against culture time.

The cytotoxic effect of hLL1 was compared with that of mLL1 and cLL1 in Raji cells, a human lymphoma cell line. Goat anti-human IgG Fc fragment specific Ab (α-hFc) was used as the crosslinker for hLL1 and cLL1 and goat anti-mouse IgG Fc specific Ab (α-mFc) was used for mLL1. $5 \times 10^5$ Raji cells were seeded at day 0 in 1 ml of culture medium containing 5 μg/ml of a LL1 Ab and 50 μg/ml of the appropriate crosslinker. The numbers of total and viable cells were counted daily for 3 days. As shown in FIG. 11, The total number of normal Raji cells increased 4-5 fold in 3 days and cell viability remained >80% at the end of third day. Cells treated with a crosslinker alone, a LL1 Ab alone, or a LL1 Ab with an incompatible crosslinker (e.g. hLL1 and goat anti-mouse IgG Fc specific Ab), were indistinguishable from normal Raji cells. However, a combination of hLL1 and anti-human IgG Fc specific Ab effectively caused cell death: >40% reduction in cell viability in one day and almost total cell death in 3 days. The effectiveness of hLL1 was comparable with that of mLL1 and cLL1. Similar results were observed when Daudi cells were used (FIG. 12). No such effect was observed with another internalizing Ab, hLL2, (humanized anti-CD22 Ab). These results demonstrated that the cytotoxicity effect of hLL1 on lymphoma cell lines is specifically dependent on crosslinking of the Ab on the cell surface.

From the foregoing description, one skilled in the art can easily ascertain the essential characteristics of this invention, and without departing from the spirit and scope thereof, can make various changes and modifications of the invention to adapt it to various usage and conditions without undue experimentation. All patents, patent applications and publications cited herein are incorporated herein by reference in their entirety.

CITED REFERENCES

Arcamone et al., U.S. Pat. No. 4,125,607
Greenfield et al., U.S. Pat. No. 5,122,368
Janaky et al., U.S. Pat. No. 6,214,969
Kaneko et al., U.S. Pat. No. 5,349,066
Kaneko et al., U.S. Pat. No. 5,137,877
McKenzie et al., U.S. Pat. No. 5,798,097
King et al., U.S. Pat. No. 6,307,026
King et al., U.S. Pat. No. 5,824,805
King et al., U.S. Pat. No. 5,162,512
Moreland et al., U.S. Pat. No. 5,241,078
Schally et al., U.S. Pat. No. 6,184,374
Schally et al., U.S. Pat. No. 5,843,903
Willner et al., U.S. Pat. No. 5,708,146
Willner et al., U.S. Pat. No. 5,622,929
Willner et al., U.S. Pat. No. 5,606,017

OTHER REFERENCES

Anthracycline Antibiotics: New Analogs, Methods of Delivery, and Mechanisms of Action.
ACS Symposium Series 574, W. Priebe, editor, Publ. American Chemical Society, 1995.
Acton et al., J. Med. Chem., 27:638-645, 1984.
Arencibia et al., Anticancer Drugs, 12:71-78, 2001.
Benali et al., Proc. Natl. Acad. Sci. U.S.A., 97:9180-9185, 2000.
Chastzistamou et al., Clin. Cancer Res., 6:4158-4165, 2000.
Denmeade et al., Cancer Res., 58:2537-40, 1998.
Dubowchik et al., Bioconjug. Chem., 13:855-869, 2002.
Halmos et al., Cancer Lett., 136:129-136, 1999.
Hansen et al., Biochem J., 320:393-300, 1996.
Kahan et al., Breast Cancer Res. Treat., 59:255-262, 2000.
Kahan et al., Int. J. Cancer, 82:592-598, 1999.
Kahan et al., Cancer 85:2608-2615, 1999.
Kiaris et al., Eur. J. Cancer, 37:620-628, 2001.
Kiaris et al., Br. J. Cancer, 81:966-971, 1999.

Koppan et al., Cancer Res., 58:4132-4137, 1998.
Krebs et al., Cancer Res., 60:4194-4199, 2000.
Michel et al., Clin. Cancer Res., 8:2632-2639, 2002.
Miyazaki et al., Am. J. Obstet. Gynecol. 180:1095-103, 1999.
Miyazaki et al., J. Natl. Cancer Inst., 89:1803-1809, 1997.
Mosure et al., Cancer Chemother. Pharmacol., 40:251-258, 1997.
Nagy et al., Proc. Natl. Acad. Sci. U.S.A., 97:829-834, 2000.
Nagy et al., Proc. Natl. Acad. Sci. U.S.A., 95:1794-1799, 1998.
Nagy et al., Proc. Natl. Acad. Sci. USA., 94:652-656, 1997.
Nagy et al., Proc. Natl. Acad. Sci. U.S.A., 93:7269-7273, 1996.
Nagy et al., Proc. Natl. Acad. Sci, U.S.A., 93:2464-2469, 1996.
Ong et al. Immunology, 98:296-302, 1999.
Pawlyk-Byczkowska et al., Cancer Res., 49:4568-4577, 1989.
Plonowski et al., Int. J. Cancer, 88:652-657, 2000.
Plonowski et al., Cancer Res., 60:2996-3001, 2000.
Plonowski et al., Cancer Res., 59:1947-1953, 1999.
Roche et al., Proc. Natl. Acad. Sci. U.S.A., 90:8581-8585, 1993.
Schally et al., Clin. Cancer Res., 7:2854-2861, 2001.
Schally et al., Prostate, 45:158-166, 2000.
Schally et al., Eur. J. Endocrinol., 141:1-14, 1999.
Shih et al. Cancer Immunol. Immunother., 49:208-216, 2000.
Suzawa et al., J. Cont. Release, 79:229-242, 2002.
Westphalen et al., Int. J. Oncol. 17:1063-1069, 2000.
Wraight et al., J. Biol. Chem., 265:5787-5792, 1990.

What is claimed is:

1. A composition comprising a conjugate of an anthracycline drug and a humanized anti-CD74 antibody or antigen-binding fragment thereof comprising human antibody framework (FR) and constant region sequences, wherein the anthracycline drug is conjugated to the antibody or fragment thereof with 4-(N-maleimidomethyl)cyclohexane-1-carboxyl hydrazide, wherein the humanized anti-CD74 antibody competes for binding to CD74 with an LL1 antibody comprising the light chain complementarity determining region (CDR) sequences CDR1 (RSSQSLVHRNGNTYLH, SEQ ID NO:1), CDR2 (TVSNRFS, SEQ ID NO:2) and CDR3 (SQSSHVPPT, SEQ ID NO:3) and heavy chain CDR1 (NYGVN, SEQ ID NO:4), CDR2 (WINPNTGEPTFD-DDFKG, SEQ ID NO:5), and CDR3 (SRGKNEAWFAY, SEQ ID NO:6).

2. The composition of claim 1, wherein the humanized anti-CD74 antibody comprises one or more substituted FR residues selected from the group consisting of light chain variable region amino acid residues 2, 3, 4, 46, 87 and 100 of SEQ ID NO:11 and heavy chain variable region amino acid residues 5, 37, 38, 46, 68, 91 and 93 of SEQ ID NO:8.

3. The composition of claim 2, wherein the humanized anti-CD74 antibody comprises all of the light chain variable region amino acid residues 2, 3, 4, 46, 87 and 100 of SEQ ID NO:11 and heavy chain variable region amino acid residues 5, 37, 38, 46, 68, 91 and 93 of SEQ ID NO:8.

4. The composition of claim 3, wherein the humanized anti-CD74 antibody comprises the variable region amino acid sequences of SEQ ID NO:9 and SEQ ID NO:12.

5. The composition of claim 1, wherein the humanized antibody comprises human antibody constant region sequences selected from the group consisting of IgG1, IgG2a, IgG3 and IgG4.

6. The composition of claim 1, wherein said anthracycline drug is selected from the group consisting of daunorubicin, doxorubicin, epirubicin, 2-pyrrolinodoxorubicin, morpholino-doxorubicin, and cyanomorpholino-doxorubicin.

7. The composition of claim 6, wherein said anthracycline drug is linked to the antibody through the 13-keto moiety.

8. A composition comprising a conjugate of an anthracycline drug and a humanized anti-CD74 antibody or antigen-binding fragment thereof comprising human antibody framework (FR) and constant region sequences, wherein the anthracycline drug is conjugated to the antibody or fragment thereof with 4-(N-maleimidomethyl)cyclohexane-1-carboxyl hydrazide, wherein the humanized anti-CD74 antibody or antigen-binding fragment thereof is a humanized LL1 antibody or antigen-binding fragment thereof comprising light chain CDR1 having an amino acid sequence of RSSQS-LVHRNGNTYLH (SEQ ID NO:1), CDR2 having an amino acid sequence of TVSNRFS (SEQ ID NO:2) and CDR3 having an amino acid sequence of SQSSHVPPT) SEQ ID NO:3) and heavy chain CDR1 having an amino acid sequence of NYGVN (SEQ ID NO:4), CDR2 having an amino acid sequence of WINPNTGEPTFDDDFKG (SEQ ID NO:5), and CDR3 having an amino acid sequence of SRGKNEAWFAY (SEQ ID NO:6).

* * * * *

SEQUENCE LISTING

<160> NUMBER OF SEQ ID NOS: 27

<210> SEQ ID NO 1
<211> LENGTH: 16
<212> TYPE: PRT
<213> ORGANISM: Mus sp.

<400> SEQUENCE: 1

Arg Ser Ser Gln Ser Leu Val His Arg Asn Gly Asn Thr Tyr Leu His
1               5                   10                  15

<210> SEQ ID NO 2
<211> LENGTH: 7
<212> TYPE: PRT
<213> ORGANISM: Mus sp.

<400> SEQUENCE: 2

Thr Val Ser Asn Arg Phe Ser
1               5

<210> SEQ ID NO 3
<211> LENGTH: 9
<212> TYPE: PRT
<213> ORGANISM: Mus sp.

<400> SEQUENCE: 3

Ser Gln Ser Ser His Val Pro Pro Thr
1               5

<210> SEQ ID NO 4
<211> LENGTH: 5
<212> TYPE: PRT
<213> ORGANISM: Mus sp.

<400> SEQUENCE: 4

Asn Tyr Gly Val Asn
1               5

<210> SEQ ID NO 5
<211> LENGTH: 17
<212> TYPE: PRT
<213> ORGANISM: Mus sp.

<400> SEQUENCE: 5

Trp Ile Asn Pro Asn Thr Gly Glu Pro Thr Phe Asp Asp Asp Phe Lys
1               5                   10                  15

Gly

<210> SEQ ID NO 6
<211> LENGTH: 11
<212> TYPE: PRT
<213> ORGANISM: Mus sp.

<400> SEQUENCE: 6

Ser Arg Gly Lys Asn Glu Ala Trp Phe Ala Tyr
1               5                   10

<210> SEQ ID NO 7
<211> LENGTH: 120
<212> TYPE: PRT
<213> ORGANISM: Homo sapiens

<400> SEQUENCE: 7

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Ala Met Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Asp Asp Thr Ala Val Tyr Tyr Cys
                85                  90                  95

Ala Arg Glu Asp Ser Asn Gly Tyr Lys Ile Phe Asp Tyr Trp Gly Gln
            100                 105                 110

Gly Ser Leu Val Thr Val Ser Ser
        115                 120

<210> SEQ ID NO 8
<211> LENGTH: 120
<212> TYPE: PRT
<213> ORGANISM: Homo sapiens

<400> SEQUENCE: 8

Gln Val Gln Leu Gln Gln Ser Gly Pro Glu Leu Lys Lys Pro Gly Glu
1               5                   10                  15

Thr Val Lys Val Thr Cys Lys Thr Ser Gly Tyr Thr Phe Thr Asn Tyr
            20                  25                  30

Gly Val Asn Trp Ile Lys Gln Thr Pro Gly Glu Gly Leu Gln Trp Met
        35                  40                  45

Gly Trp Ile Asn Pro Asn Thr Gly Glu Pro Thr Phe Asp Asp Asp Phe
    50                  55                  60

Thr Gly Arg Phe Ala Phe Ser Leu Glu Ser Ser Ala Ser Thr Ala Phe
65                  70                  75                  80

Leu Gln Ile Ser Asn Leu Lys Asn Glu Asp Met Gly Thr Tyr Phe Cys
                85                  90                  95

Ser Arg Ser Arg Gly Lys Asn Glu Ala Trp Phe Ala Tyr Trp Gly Gln
            100                 105                 110

Gly Thr Leu Val Thr Val Ser Ser
        115                 120

<210> SEQ ID NO 9
<211> LENGTH: 120
<212> TYPE: PRT

<213> ORGANISM: Homo sapiens

<400> SEQUENCE: 9

```
Gln Val Gln Leu Gln Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Val Asn Trp Ile Lys Gln Ala Pro Gly Gln Gly Leu Gln Trp Met
        35                  40                  45

Gly Trp Ile Asn Pro Asn Thr Gly Glu Pro Thr Phe Asp Asp Asp Phe
    50                  55                  60

Thr Gly Arg Phe Ala Phe Ser Leu Asp Thr Ser Val Ser Thr Ala Tyr
65                  70                  75                  80

Leu Gln Ile Ser Ser Leu Lys Ala Asp Asp Thr Ala Val Tyr Phe Cys
                85                  90                  95

Ser Arg Ser Arg Gly Lys Asn Glu Ala Trp Phe Ala Tyr Trp Gly Gln
            100                 105                 110

Gly Ser Leu Val Thr Val Ser Ser
        115                 120
```

<210> SEQ ID NO 10
<211> LENGTH: 111
<212> TYPE: PRT
<213> ORGANISM: Homo sapiens

<400> SEQUENCE: 10

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Phe Thr Phe Gly Gln Gly Thr Arg Leu Glu Ile
            100                 105                 110
```

<210> SEQ ID NO 11
<211> LENGTH: 113
<212> TYPE: PRT
<213> ORGANISM: Homo sapiens

<400> SEQUENCE: 11

```
Asp Ile Gln Leu Thr Gln Thr Pro Leu Ser Leu Pro Val Ser Leu Asp
1               5                   10                  15

Gln Pro Ala Ser Ile Ser Cys Arg Ser Ser Gln Ser Leu Val His Arg
            20                  25                  30

Asn Gly Asn Thr Tyr Leu His Trp Tyr Leu Gln Arg Pro Gly Gln Ser
        35                  40                  45

Pro Lys Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80
```

```
Ser Arg Val Glu Ala Glu Asp Leu Gly Val Tyr Phe Cys Ser Gln Ser
            85                  90                  95

Ser His Val Pro Pro Thr Phe Gly Ala Gly Thr Lys Leu Glu Ile Lys
            100                 105                 110
Arg

<210> SEQ ID NO 12
<211> LENGTH: 113
<212> TYPE: PRT
<213> ORGANISM: Homo sapiens

<400> SEQUENCE: 12

Asp Ile Gln Leu Thr Gln Ser Pro Leu Ser Leu Pro Val Thr Leu Gly
1               5                   10                  15

Gln Pro Ala Ser Ile Ser Cys Arg Ser Ser Gln Ser Leu Val His Arg
            20                  25                  30

Asn Gly Asn Thr Tyr Leu His Trp Phe Gln Gln Arg Pro Gly Gln Ser
        35                  40                  45

Pro Arg Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Ser His Val Pro Pro Thr Phe Gly Ala Gly Thr Arg Leu Glu Ile Lys
            100                 105                 110
Arg

<210> SEQ ID NO 13
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(360)

<400> SEQUENCE: 13 cag gtc caa ctg cag caa tct ggg tct gag ttg aag aag cct ggg gcc      48
Gln Val Gln Leu Gln Gln Ser Gly Ser Glu Leu Lys Lys Pro Gly Ala
1               5                   10                  15 tca gtg aag gtt tcc tgc aag gct tct gga tac acc ttc act aac tat      96
Ser Val Lys Val Ser Cys Lys Ala Ser Gly Tyr Thr Phe Thr Asn Tyr
            20                  25                  30 gga gtg aac tgg ata aag cag gcc cct gga caa ggg ctt cag tgg atg     144
Gly Val Asn Trp Ile Lys Gln Ala Pro Gly Gln Gly Leu Gln Trp Met
        35                  40                  45 ggc tgg ata aac ccc aac act gga gag cca aca ttt gat gat gac ttc     192
Gly Trp Ile Asn Pro Asn Thr Gly Glu Pro Thr Phe Asp Asp Asp Phe
    50                  55                  60 aag gga cga ttt gcc ttc tcc ttg gac acc tct gtc agc acg gca tat     240
Lys Gly Arg Phe Ala Phe Ser Leu Asp Thr Ser Val Ser Thr Ala Tyr
65                  70                  75                  80 ctc cag atc agc agc cta aag gct gac gac act gcc gtg tat ttc tgt     288
Leu Gln Ile Ser Ser Leu Lys Ala Asp Asp Thr Ala Val Tyr Phe Cys
                85                  90                  95 tca aga tcg agg ggt aaa aac gaa gcc tgg ttt gct tat tgg ggc caa     336
Ser Arg Ser Arg Gly Lys Asn Glu Ala Trp Phe Ala Tyr Trp Gly Gln
            100                 105                 110
```

```
ggg acc ctg gtc acc gtc tcc tca                                    360
Gly Thr Leu Val Thr Val Ser Ser
        115                 120

<210> SEQ ID NO 14
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Val Gln Leu Gln Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Val Asn Trp Ile Lys Gln Ala Pro Gly Gln Gly Leu Gln Trp Met
        35                  40                  45

Gly Trp Ile Asn Pro Asn Thr Gly Glu Pro Thr Phe Asp Asp Asp Phe
    50                  55                  60

Lys Gly Arg Phe Ala Phe Ser Leu Asp Thr Ser Val Ser Thr Ala Tyr
65                  70                  75                  80

Leu Gln Ile Ser Ser Leu Lys Ala Asp Asp Thr Ala Val Tyr Phe Cys
                85                  90                  95

Ser Arg Ser Arg Gly Lys Asn Glu Ala Trp Phe Ala Tyr Trp Gly Gln
            100                 105                 110

Gly Thr Leu Val Thr Val Ser Ser
        115                 120

<210> SEQ ID NO 15
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(339)

<400> SEQUENCE: 15 gac atc cag ctg act cag tct cca ctc tcc ctg ccc gtc acc ctt gga    48
Asp Ile Gln Leu Thr Gln Ser Pro Leu Ser Leu Pro Val Thr Leu Gly
1               5                   10                  15 cag ccg gcc tcc atc tcc tgc aga tca agt cag agc ctt gta cac aga    96
Gln Pro Ala Ser Ile Ser Cys Arg Ser Ser Gln Ser Leu Val His Arg
            20                  25                  30 aat gga aac acc tat tta cat tgg ttt cag cag agg cca ggc caa tct   144
Asn Gly Asn Thr Tyr Leu His Trp Phe Gln Gln Arg Pro Gly Gln Ser
        35                  40                  45 cca agg ctc ctg atc tac aca gtt tcc aac cga ttt tct ggg gtc cca   192
Pro Arg Leu Leu Ile Tyr Thr Val Ser Asn Arg Phe Ser Gly Val Pro
    50                  55                  60 gac aga ttc agc ggc agt ggg tca ggc act gat ttc aca ctg aaa atc   240
Asp Arg Phe Ser Gly Ser Gly Ser Gly Thr Asp Phe Thr Leu Lys Ile
65                  70                  75                  80 agc agg gtg gag gct gag gat gtt ggg gtt tat ttc tgc tct caa agt   288
Ser Arg Val Glu Ala Glu Asp Val Gly Val Tyr Phe Cys Ser Gln Ser
                85                  90                  95 tca cat gtt cct ccc acg ttc ggt gct ggg aca cga ctg gag atc aaa   336
Ser His Val Pro Pro Thr Phe Gly Ala Gly Thr Arg Leu Glu Ile Lys
```

```
                                                                  339
cgt
Arg <210> SEQ ID NO 16
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Asp Ile Gln Leu Thr Gln Ser Pro Leu Ser Leu Pro Val Thr Leu Gly
1               5                   10                  15

Gln Pro Ala Ser Ile Ser Cys Arg Ser Ser Gln Ser Leu Val His Arg
            20                  25                  30

Asn Gly Asn Thr Tyr Leu His Trp Phe Gln Gln Arg Pro Gly Gln Ser
        35                  40                  45

Pro Arg Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Ser His Val Pro Pro Thr Phe Gly Ala Gly Thr Arg Leu Glu Ile Lys
            100                 105                 110

Arg

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gatgttcagc tgacccaaac tccactctcc                                   30

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cagatccagc tgcagcagtc tggacctgag                                   30

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gagacggtga ccagagtccc ttggccccaa                                   30

<210> SEQ ID NO 20
```

<211> LENGTH: 176
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 20
ggtctgagtt gaagaagcct ggggcctcag tgaaggtttc ctgcaaggct tctggataca      60
ccttcactaa ctatggagtg aactggataa agcaggcccc tggacaaggg cttcagtgga     120
tgggctggat aaaccccaac actggagagc caacatttga tgatgacttc aaggga         176

<210> SEQ ID NO 21
<211> LENGTH: 165
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 21
tcccttggcc ccaataagca aaccaggctt cgtttttacc cctcgatctt gaacagaaat      60
acacggcagt gtcgtcagcc tttaggctgc tgatctggag atatgccgtg ctgacagagg     120
tgtccaagga gaaggcaaat cgtcccttga agtcatcatc aaatg                     165

<210> SEQ ID NO 22
<211> LENGTH: 38
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 22
gtggtgctgc agcaatctgg gtctgagttc aagaagct                              38

<210> SEQ ID NO 23
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 23
aagtggatcc tataatcatt cctaggatta atg                                   33

<210> SEQ ID NO 24
<211> LENGTH: 159
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 24
cagtctccac tctccctgcc cgtcaccctt ggacagccgg cctccatctc ctgcagatca      60
agtcagagcc ttgtacacag aaatggaaac acctatttac attggtttca gcagaggcca     120
ggccaatctc caaggctcct gatctacaca gtttccaac                             159

<210> SEQ ID NO 25
<211> LENGTH: 169
<212> TYPE: DNA
<213> ORGANISM: Artificial Sequence -continued

```
<220> FEATURE:
<223> OTHER INFORMATION: Description of Artificial Sequence: Synthetic
      polynucleotide

<400> SEQUENCE: 25
tgtcccagca ccgaacgtgg gaggaacatg tgaactttga gagcagaaat aaaccccaac      60
atcctcagcc tccaccctgc tgattttcag tgtgaaatca gtgcctgacc cactgccgct     120
gaatctgtct gggaccccag aaaatcggtt ggaaactgtg tagatcagg                  169

<210> SEQ ID NO 26
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gatgttcagc tgactcagtc tccactctcc ctg                                   33

<210> SEQ ID NO 27
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gttagatctc cagtcgtgtc ccagcaccga acg                                   33
```